(12) United States Patent
Katayama et al.

(10) Patent No.: US 8,304,520 B2
(45) Date of Patent: Nov. 6, 2012

(54) LABELED FUSION PROTEIN

(75) Inventors: Eisaku Katayama, Tokyo (JP); Takashi Murayama, Tokyo (JP); Taku Kashiyama, Tokyo (JP); Takuya Kobayashi, Tokyo (JP)

(73) Assignees: The University of Tokyo, Tokyo (JP); Juntendo University, Tokyo (JP)

( * ) Notice: Subject to any disclaimer, the term of this patent is extended or adjusted under 35 U.S.C. 154(b) by 291 days.

(21) Appl. No.: 12/517,964

(22) PCT Filed: Dec. 5, 2007

(86) PCT No.: PCT/JP2007/073482
§ 371 (c)(1),
(2), (4) Date: Jun. 5, 2009

(87) PCT Pub. No.: WO2008/069232
PCT Pub. Date: Jun. 12, 2008

(65) Prior Publication Data
US 2010/0105882 A1  Apr. 29, 2010

(30) Foreign Application Priority Data
Dec. 8, 2006 (JP) .................. 2006-332530

(51) Int. Cl.
C07K 14/00 (2006.01)
C07K 1/00 (2006.01)
C12P 21/06 (2006.01)
(52) U.S. Cl. ........ 530/350; 530/300; 530/412; 435/69.1
(58) Field of Classification Search .................. None
See application file for complete search history.

(56) References Cited

U.S. PATENT DOCUMENTS
2003/0170230 A1* 9/2003 Caterer et al. ............. 424/130.1

FOREIGN PATENT DOCUMENTS
JP   2006-343207 A   12/2006
WO  WO 02/10418   *  2/2002

OTHER PUBLICATIONS

Song et al. Engineered single-chain, antiparallel, coiled coil mimics the MerR metal binding site. J. Bacteriol. Mar. 2004, 186 (6) 1861-1868.*

Khan, Farid et al., *Analytical Chemistry*, vol. 78, No. 9 (2006) pp. 3072-3079.
Routzahn, Karen M. et al., *J. of Structural and Functional Genomics*, vol. 2, No. 2 (2002) pp. 83-92.
Oakley, Martha G. et al., *Current Opinion in Structural Biology*, vol. 11, No. 4 (2001) pp. 450-457.
Katayama, "Bunshi o Miru: Denshi Kenbikyo ni yoru Tanpakushitsu Fukugotai no Kansatsuho", Cell Technology, Apr. 2007, vol. 26, pp. 438 to 443.
Gibbons et al., "The Affinity of the Dynein Microtubule-binding Domain is Modulated by the Conformation of its Coiled-coil Stalk", The Journal of Biological Chemistry, 2005, vol. 280, pp. 23960-23965.
Djinovic-Carugo et al., "Structure of alpha-Actinin Rod: Molecular Basis for Cross-Linking of Actin Filaments", Cell, Aug. 20, 1999, vol. 98, pp. 537-546.
Smith et al., "Clathrin: anatomy of a coat protein", Trends in Cell Biology, Sep. 1999, vol. 9, pp. 335-338.
Medalia et al., "Macromolecular Architecture in Eukaryotic Cells Visualized by Cryoelectron Tomography", Science, Nov. 8, 2002, vol. 298, pp. 1209-1213.
Katayama et al., "Native Structure and arrangement of inositol-1,4,5-trisphosphate receptor molecules in bovine cerebellar Purkinje cells as studied by quick-freeze deep-etch electron microscopy", The EMBO Journal, 1996, vol. 15, No. 18, pp. 4844-4851.
Bourguignon Lyw et al., J. Biol. Chem., vol. 275 (2000) pp. 1829-1838.
European Examination Report issued in European Patent Application No. 07859710.1 on Apr. 12, 2011.
European Examination Report issued in European Application No. 07 859 710.1 on Jul. 14, 2011.
Kapiloff et al., "mAKAP: an A-kinase anchoring protein targeted to the nuclear membrane of differentiated myocytes", J. Cell Sci., vol. 112 (1999) pp. 2725-2736.

* cited by examiner

*Primary Examiner* — Nashaat Nashed
(74) *Attorney, Agent, or Firm* — Birch Stewart Kolasch & Birch, LLP

(57) ABSTRACT

The present invention aims at providing a general-purpose experimental tool which specifically binds to a macromolecular substance that will be a receptor for a specific ligand such as drug, and is applicable throughout various processes to explore the nature of the macromolecular substance. In order to achieve this object, a molecular module has been developed which binds to a target compound and is used for purifying or labeling the target compound, wherein the molecular module has a rod-like spacer substance, an interacting substance that interacts with the target compound, a tag and a labeling substance, the interacting substance being positioned at one end of the rod-like spacer substance, and the tag and the labeling substance being positioned at the other end of the rod-like spacer substance.

11 Claims, 12 Drawing Sheets

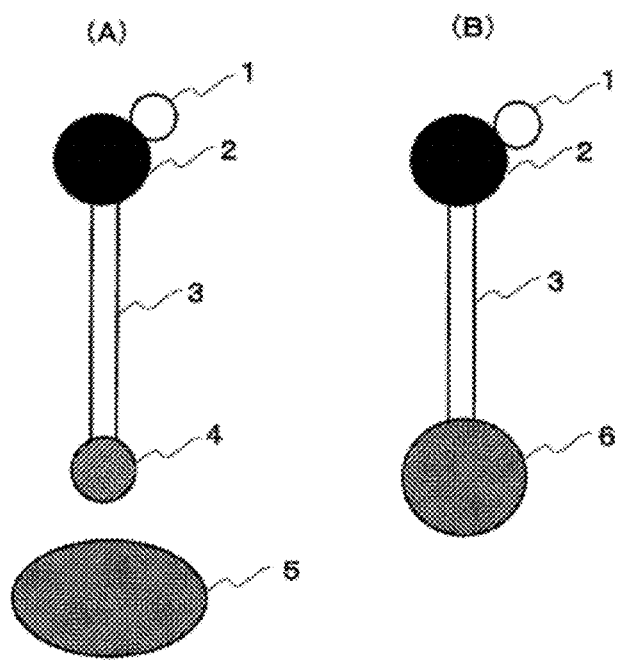

VDQLKIKVEQLKEKVNELELENDELKAKVDNLNSKNRELDVKNEQANQKLKQLVQDVQA
AEIKVKDASELQVQLDVRNKEIAVQKVKAHADLEKAEPAIIEGSGVSKGEELPTGVVP
ILVELDGDVNGHKFSVSGEGEGDATYGKLTLKFICTTGKLPVPWPTLVTTLTYGVQCFS
RYPDHMKQHDFFKSAMPEGYVQERTIFFKDDGNYKTRAEVKFEGDTLVNRIELKGIDFK
EDGNILGHKLEYNYNSHNVYIMADKQKNGIKVNFKIRHNIEDGSGHHHHHHHGSGAG
TPVTAFLAGTINKVLASEGQTVAAGEVLLILEAMKMETEIRAAQAGTVRGIAVKAGDAV
AVGDTLMTLAGSGSHGSGEVQLADHYQQNTPIGDGPVLLPDNHYLSTQSALSKDPNEK
RDHMVLLEPVTAAGITLGMDELYKGSGSEILDRIKPLRKEEVEQLENAANELKLKQDEI
VATITALEKSIASLKEEVATLIRETEQIKTESSKVKAQVQALEIEVKDNKTKVVQLEVE
VAQLESEVKDLE

Fig. 3

VDQLKIKVEQLKEKVNELELENDELKAKVDNLNSKNRELDVKNEQANQKLKQLVQDVQA
AEIKVKDASELQVQLDVRNKEIAVQKVKAHADLEKAEPAIIEGSGDNTEDVIKEFMQF
KVRMEGSVNGHYFEIEGEGEGKPYEGTQTAKLQVTKGGPLPFAWDILSPQFQYGSKAYV
KHPADIPDYMKLSFPEGFTWERSMNFEDGGVVEVQQDSSLQDGTFIYKVKFKGVNFPAD
GPVMQKKTAGWEPSTEKLYPQDGVLKGEISHALKLEDGSGHHHHHHHGSGAGTPVTA
PLAGTIWKVLASEGQTVAAGEVLLILEAMKMETEIRAAQAGTVRGIAVKAGDAVAVGDT
LMTLAGSGSHYTCDPKTVYKAKKPVQLPGNHYVDSKLDITNHNEDYTVVEQYEHAEAR
HSGSQSGSEILDRIKPLREEVEQLENAANELKLKQDEIVATITALEKSIASLKEEVAT
LIRETEQIKTESSKVKAQVQALEIEVKDNKTKVVQLEVEVAQLESEVKDLE

Fig. 4

VDQLKIKVEQLKEKVNELELENDELKAKVDNLNSKNRELDVKNEQANQKLKQLVQDVQA
VRIKSQELEVKNAAANDKLKKMVKDQQEAEKKKVMSQEIQEQLHKQQEVIADKQMSVKE
DLDKAEIKVKDASELQVQLDVRNKEIAVQKVKAHADLEKAEPAIIEGSGVSKGEELFT
GVVPILVELDGDVNGHKFSVSGEGEGDATYGKLTLKFICTTGKLPVPWPTLVTTLTYGV
QCFSRYPDHMKQHDFFKSAMPEGYVQERTIFFKDDGNYKTRAEVKFEGDTLVNRIELKG
IDFKEDGNILGHKLEYNYNSHNVYIMADKQKNGIKVNFKIRHNIEDGSGHHHHHHHG
SGAGTPVTAPLAGTIWKVLASEGQTVAAGEVLLILEAMKMETEIRAAQAGTVRGIAVK
AGDAVAVGDTLMTLAGSGSHQSQSVQLADHYQQNTPIGDGPVLLPDNHYLSTQSALSK
DPNEKRDHMVLLEFVTAAGITLGMDELYKGSGSEILDRIKPLREEVEQLENAANELKL
KQDEIVATITALEKSIASLRNELQKLEDDAKDNQQKANEVEQMIRDLEASIARYKEEYA
VLISEAQAIKADLAAVEAKVKSLKEEVATLIRETEQIKTESSKVKAQVQALEIEVKDNK
TKVVQLEVEVAQLESEVKDLE

Fig. 5

VDQLKIKVEQLKEKVNELELENDELKAKVDNLNSKNRELDVKNEQANQKLKQLVQDVQA
VRIKSQELEVKNAAANDKLKKMVKDQQEAEKKKVMSQEIQEQLHKQQEVIADKQMSVKE
DLDKAEIKVKDASELQVQLDVRNKEIAVQKVKAHADLEKAEPAIIEGSQDNTEDVIKE
FMQFKVRMEGSVNGHYFEIEGEGEGKPYEGTQTAKLQVTKGGPLPFAWDILSPQFQYGS
KAYVKHPADIPDYMKLSFPEGFTWERSMNFEDGGVVEVQQDSSLQDGTFIYKVKFKGVN
FPADGPVMQKKTAGWEPSTEKLYPQDGVLKGEISHALKLKDGSQHHHHHHHHGSGAGT
PVTAPLAGTIWKVLASEGQTVAAGEVLLILEAMKMETEIRAAQAGTVRGIAVKAGDAVA
VGDTLMTLAGSGSHYTCDFKTVYKAKKPVQLPGNHYVDSKLDITNHNEDYTVVEQYER
AEARHSGSQSGSEILDRIKPLREEVEQLENAANELKLKQDEIVATITALEKSIASLRN
ELQKLEDDAKDNQQKANEVEQMIRDLEASIARYKEEYAVLISEAQAIKADLAAVEAKVK
SLKEEVATLIRETEQIKTESSKVKAQVQALEIEVKDNKTKVVQLEVEVAQLESEVKDLE

Fig. 6

ELNQENEQLMEDYEKLASDLLEWIRRTIPWLENRAPENTMQAMQQKLEDFRDYRRLHKPPKV
QEKCQLEINFNTLQTKLRLSNRPAFMPSEGKMVSDINNAWGGLEQAEKGYEEWLLNEIRRLE
RLDHLAEKFRQKASIKESWTDGKEAMLQQKDYETATLSEIKALLKKHEAFESDLAAHQDRVE
QIAAIAQELNELDYYDSPSVNARCQKICDQWDNLGALTQKRREALERTEKLLETIDQLYLEY
AKRAAPFNNWMEGAMEDLQDTFIVHTIEEIQGLTTAHEQFKATLPDADKERQAILGIHNEVS
KIVQTYHVNMAGTNPYTTITPQEINGKWEHVRQLVFRRDQALMEEHARQQQNERLRKQPGAQ
ANVIGPWIQTKMEEIGRISIEMHGTLEDQLNHLRQYEKSIVNYKPKIDQLEGDHQQIQEALI
FDNKHTNYTMEHIRVGWEQLLTPTIARTINEVENQILTLEGSQVSKGEELFTGVVPILVELDG
DVNGHKFSVSGEGEGDATYGKLTLKFICTTGKLPVPWPTLVTTLTYGVQCFSRYPDHMKQHD
FFKSAMPEGYVQERTIFFKDDGNYKTRAEVKFEGDTLVNRIELKGIDFKEDGNILGHKLEYN
YNSHNVYIMADKQKNGIKVNFKIRHNIEDSQHHHHHHHHGSGAGTPVTAPLAGTIWKVLASE
GQTVAAGEVLLILEAMKMETEIRAAQAGTVRGIAVKAGDAVAVGDTLMTLAGSGSHGSGSVQ
LADHYQQNTPIGDGPVLLPDNHYLSTQSALSKDPNEKRDHMVLLEFVTAAGITLGMDELYKG
SGSEVD

Fig. 7
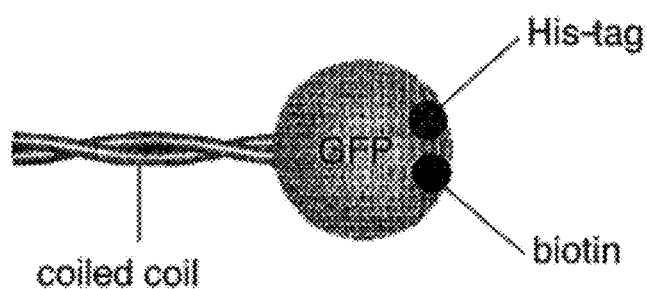
Fig. 8
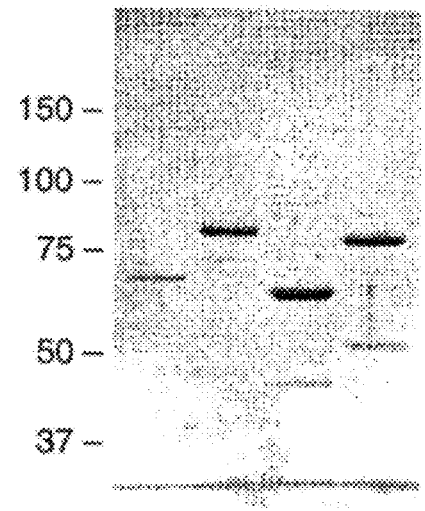
Streptavidin HRP

Fig. 11
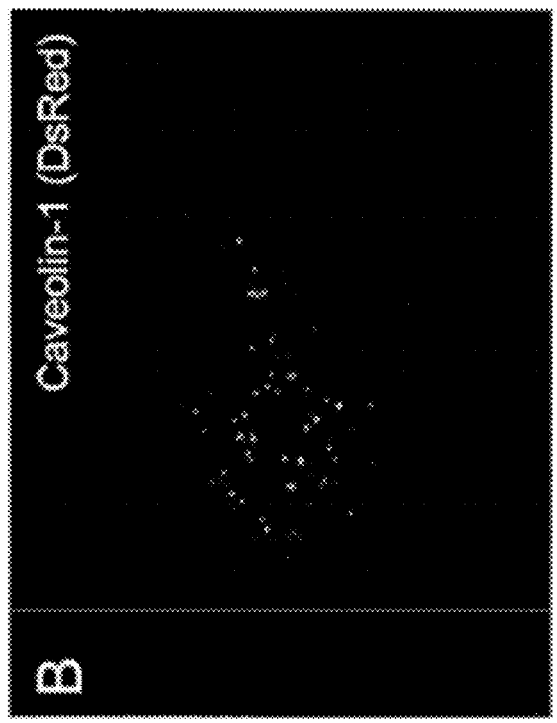
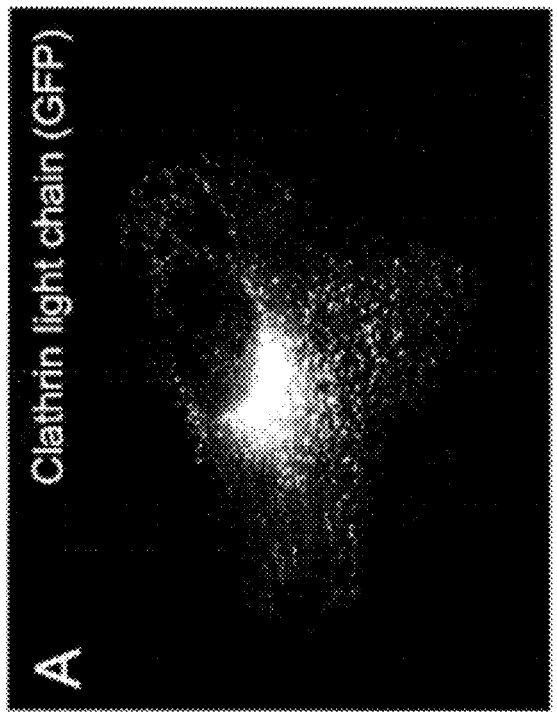

GFP-short-IP$_3$R1     His-IP$_3$R1

Fig. 14
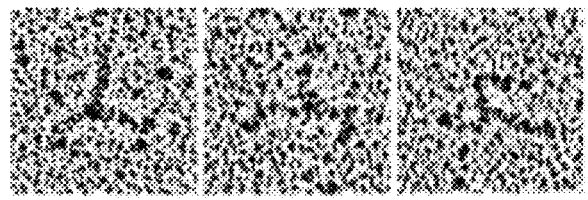
Control
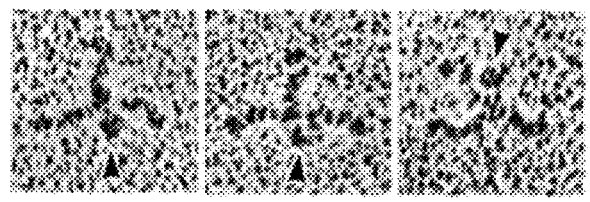
Short
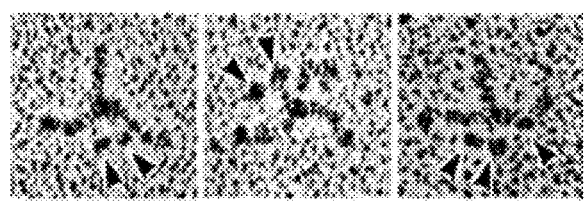
Long
Fig. 15
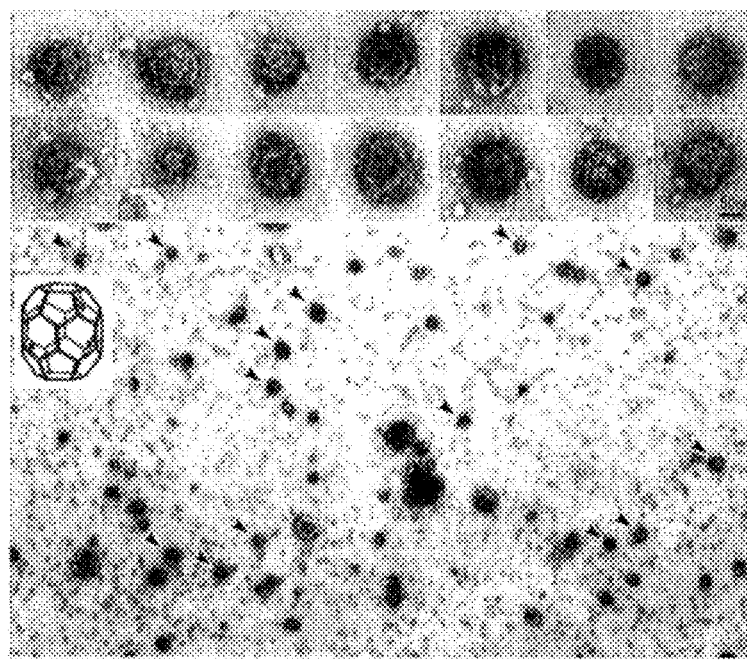

Fig. 19

TIDQLHLEFAKRAAPFNNWMEGAMEDLQDMFIVHSIEEIQSLISAHDQFKATLPEADGE
RQAILSIQMEVEKVIQSYSMRISASNPYSTVTVEEIRTKWEKVKQLVPQRDQSLQEELA
RQHAMERLRRQFAAQANVIGPWIQTKMEEIARSSIEMTGPLEDQMNQLKQYEQNIINYK
HNIDKLEGDHQLIQEALVFDNKHTNYTMEHIRVGWELLLTTIARTINEVETQILTEFG
SGVSKGEELFTGVVPILVELDGDVNGHKFSVSGEGEGDATYGKLTLKFICTTGKLPVP
WPTLVTTLTYGVQCFSRYPDHMKQHDFFKSAMPEGYVQERTIFFKDDGNYKTRAEVKFE
GDTLVNRIELKGIDFKEDGNILGHKLEYNYNSHNVYIMADKQKNGIKVNFKIRHNIEDG
SGHHHHHHGSGAGTPVTAPLAGTIWKVLASEGQTVAAGEVLLILEAMKMETEIRAA
QAGTVRGIAVKAGDAVAVGDTLMTLASSGSHGSGSVQLADHYQQNTPIGDGPVLLPDN
HYLSTQSALSKDPNEKRDHMVLLEFVTAAGITLGMDELYKGSGSVDNQENERLMEEYE
RLASELLEWIRRTIPWLENRTPEKTMQAMQKKLEDFRDYRRKHKPPKVQEKCQLEINFN
TLQTKLRISNRPAFMPSEGRMVSDIAGAWQRLEQAERGYEEWLLNEIRRLERLEHLAEK
FRQKASTHEQWAYGKEQILLQKDYESASLTEVRAMLRKHEAFESDLAAHQDRVEQIAAI
AQELNELDYHDAASVNDRCQKICDQWDSLGTLTQKEREALERTEKLLE

LABELED FUSION PROTEIN

TECHNICAL FIELD

The present invention relates to a molecular module for purifying or labeling a target compound; a tag and a label-fused protein based on the molecular module; and a method of protein purification using the molecular module.

BACKGROUND ART

In order to explore the nature of a molecule that could be a receptor for a specific ligand (such as physiologically active substance, drug or antibody that acts upon binding to a cell composing, macromolecular component, e.g., protein or nucleic acid), usually, several techniques selected from various existing technologies are used in combination. For example, various techniques such as a technique of identifying an unknown receptor by such as photoaffinity labeling using a drug derivative or the like as a ligand; a technique of the intracellular localization of the receptor; a technique of isolating/purifying the receptor and examining its nature; or a technique of elucidating the binding site within the receptor (complex) molecule with a higher spatial resolution must be used jointly as the purpose demands. Even when one ligand is to be investigated, it is necessary to prepare separately a number of ligand derivatives suitable for individual techniques, which imposes a tremendous burden.

As a method of identifying those components to which a specific drug binds, affinity labeling is known. In this method, a ligand derivative to which a fluorescent dye or radioactive isotope has been added is photo-crosslinked to a target. Subsequently, information such as the molecular weight or amino acid sequence of the resultant labeled molecule is obtained using electrophoresis or various chromatographies.

For isolation and purification of a substance which will be a target binding partner for a ligand (such as receptor), a series of techniques called affinity purification is often used. When the target is a protein or a complex thereof, the classical chromatography is usually used in which resin beads immobilizing a ligand by covalent bond are packed in a column; a raw solution containing the target material is applied to the column; and the bound fractions alone are dissociated and eluted. However, when the target is a large-sized membrane fraction or non-adherent cell each of which is difficult to apply to the column, a batch method is also used in which similar resin beads or magnetic beads are utilized to collect the target substance by centrifugation or magnetism. In particular, when a target substance is to be separated after binding to a protein that is embedded in the membrane (such as intracellular organelle or non-adherent cell), a ligand directly immobilized on the surfaces of resin or magnetic beads is difficult to contact the target substance in many cases. In order to solve this problem, a spacer consisting of long straight carbon chain is inserted between the beads and the ligand. However, when a long carbon chain is used, hydrophobicity often increases. This makes it highly possibility that the binding of the target substance by the ligand does not necessarily reflect their specificity. For alleviation of this problem, it is desirable to use a spacer capable of always retaining a long distance.

On the other hand, in order to microscopically indicate the intracellular or extracellular localization site of a ligand-binding protein, a part or the whole of the protein prepared by a biochemical or molecular biological technique is used to prepare a specific antibody. Then, the localization (site) of the protein is elucidated by immunofluorescence or immunoelectron microscopy using the antibody. Further, for searching the binding site within the target molecule (complex), conventionally, structural data are collected by those means capable of obtaining atomic resolution, e.g., purifying and crystallizing the receptor/ligand complex and subjecting the crystal to X ray diffraction.

Although comprehensive methods to explore a large number of materials have been invented (e.g., use of robots), basically, researchers have no choice but to combine these techniques and proceed step by step in order to achieve their initial purpose. Regardless of what processes are employed, it is necessary to prepare individual ligands suitable for selected techniques. This always imposes a considerable burden in terms of labor, time and cost.

[Patent Document 1] Japanese Unexamined Patent Publication No. 2005-291836

DISCLOSURE OF THE INVENTION

Problem for Solution by the Invention

Under the above-described circumstances, a convenient material which does not affect the specific affinity between ligand and receptor and thus can be used throughout all the exploring processes will be able to reduce the above-mentioned burden greatly. It is desired to make full use of protein engineering or organic chemistry to thereby develop a general-purpose protein module that can be used for such a purpose. In reply to this demand, the present invention aims to provide a general-purpose experimental tool which specifically binds to a macromolecular substance that will be a receptor for a specific ligand such as drug, and is applicable throughout various processes to characterize the properties of the macromolecular substance.

Means to Solve the Problem

As a result of extensive and intensive researches toward the solution of the above-described problem, the present inventors have found that by adding to a target compound to be explored a tag and a label through a rod-like spacer substance, it is possible to give a molecular module a form suitable for wide-ranged exploration techniques (such as identification, isolation, microscopic observation, etc.) without altering the nature of the target compound.

It is also possible to add a tag and a label directly to a target substance. For example, the following methods may be contemplated; a method in which the target compound to be explored is fused to a tag and a label, and a method in which a substance with affinity for the target compound is added to both tag and label, and the resultant tag and label are bound to the target compound. However, the former method involves a possibility that the insertion of tag and label may destroy or alter the conformation of the target compound, resulting in the loss of the inherent nature of the target compound. In the latter method, the label and the tag may not bind to the target compound well due to steric hindrance of the target compound or compounds adjacent thereto. Even when the label and the tag could bind to the target compound, they may not be sufficiently exposed from the surface to the target compound, resulting in insufficient function as a tag and a label.

The present invention has been achieved based on the above-described findings.

The present invention provides the following (1) to (14).
(1) A molecular module which binds to a target compound and is used for purifying or labeling the target compound, wherein the molecular module has a rod-like spacer substance, an interacting substance that interacts with the target compound, a tag and a labeling substance, the interacting substance being positioned at one end of the rod-like spacer substance, and the tag and the labeling substance being positioned at the other end of the rod-like spacer substance.

(2) The molecular module according to (1), wherein the rod-like spacer substance, the interacting substance, the tag and the labeling substance form a polypeptide chain.

(3) The molecular module according to (1) or (2), wherein the rod-like spacer substance is a protein that takes an antiparallel coiled coil structure or a protein that takes a spectrin repeat structure.

(4) The molecular module according to any one of (1) to (3), wherein the tag is a histidine tag or a biotin acceptor peptide.

(5) The molecular module according to any one of (1) to (4), wherein the labeling substance is GFP or DsRed.

(6) A tag and a label-fused protein having a protein body, a rod-like spacer substance, a tag and a labeling substance, wherein the protein body is positioned at one end of the rod-like spacer substance, and the tag and the labeling substance are positioned at the other end of the rod-like spacer substance.

(7) The tag and label-fused protein according to (6), wherein the protein body, the rod-like spacer substance, the tag and the labeling substance form a polypeptide chain.

(8) The tag and label-fused protein according to (6) or (7), wherein the rod-like spacer substance is a protein that takes an antiparallel coiled coil structure or a protein that takes a spectrin repeat structure.

(9) The tag and label-fused protein according to any one of (6) to (8), wherein the tag is a histidine tag or a biotin acceptor peptide.

(10) The tag and label-fused protein according to any one of (6) to (9), wherein the labeling substance is GFP or DsRed.

(11) A method of protein purification comprising the following steps:

(i) a step of expressing a fusion protein-encoding DNA in a cell, wherein the fusion protein has a protein body, a rod-like spacer substance, a tag and a labeling substance, the protein body being positioned at one end of the rod-like spacer substance, and the tag and the labeling substance being positioned at the other end of the rod-like spacer substance;

(ii) a step of disrupting the cell and contacting the resultant homogenate with a substance having affinity for the tag; and (iii) a step of collecting the fusion protein bound to the substance having affinity to the tag.

(12) The method according to (11), wherein the rod-like spacer substance is a protein that takes an antiparallel coiled coil structure or a protein that takes a spectrin repeat structure.

(13) The method according to (11) or (12), wherein the tag is a histidine tag or a biotin acceptor peptide.

(14) The method according to any one of (11) to (13), wherein the labeling substance is GFP or DsRed.

Effect of the Invention

Conventionally, for exploring the properties of a substance, it was necessary to convert a target substance into a form suitable for each of the exploring techniques selected. However, by using the molecular module of the present invention, it becomes possible to omit such complicated operations.

BRIEF DESCRIPTION OF THE DRAWINGS

FIG. 1 shows a schematic diagram of the molecular module of the present invention (A) and a schematic diagram of the tag and label-fused protein of the present invention (B).

FIG. 2 shows the amino acid sequence (SEQ ID NO:1) of a fusion protein comprising a protein based on the stalk domain of dynein having a mutation introduced thereinto (a short-type protein of rod-like spacer structure is used; hereafter, a protein of this type is referred to as the "short type"), a histidine tag, a biotin acceptor peptide and GFP. The portion marked with a single underline is GFP; the portion marked with a double underline is the biotin acceptor peptide; the portion marked with a dotted underline is the histidine tag; the portions enclosed with boxes are linkers; and the portions without any marking represent the dynein protein whose stalk domain has been mutated.

FIG. 3 shows the amino acid sequence (SEQ ID NO:2) of a fusion protein comprising a protein based on the stalk domain of dynein having a mutation introduced thereinto (short type), a histidine tag, a biotin acceptor peptide and DsRed. The portion marked with a single underline is DsRed; the portion marked with a double underline is the biotin acceptor peptide; the portion marked with a dotted underline is the histidine tag; the portions enclosed with boxes are linkers; and the portions without any marking represent the dynein protein whose stalk domain has been mutated.

FIG. 4 shows the amino acid sequence (SEQ ID NO:3) of a fusion protein comprising a protein based on the stalk domain of dynein having a mutation introduced thereinto (a long-type protein of rod-like spacer structure is used; hereinafter, a protein of this type is referred to as the "long type"), a histidine tag, a biotin acceptor peptide and GFP. The portion marked with a single underline is GFP; the portion marked with a double underline is the biotin acceptor peptide; the portion marked with a dotted underline is the histidine tag; the portions enclosed with boxes are linkers; and the portions without any marking represent the dynein protein whose stalk domain has been mutated.

FIG. 5 shows the amino acid sequence (SEQ ID NO:4) of a fusion protein comprising a protein based on the stalk domain of dynein having a mutation introduced thereinto (long type), a histidine tag, a biotin acceptor peptide and DsRed. The portion marked with a single underline is DsRed; the portion marked with a double underline is the biotin acceptor peptide; the portion marked with a dotted underline is the histidine tag; the portions enclosed with boxes are linkers; and the portions without any marking represent the dynein protein whose stalk domain has been mutated.

FIG. 6 shows the amino acid sequence (SEQ ID NO:5) of a fusion protein comprising the rod domain of one polypeptide chain of α-actinin, a histidine tag, a biotin acceptor peptide and GFP. The portion marked with a single underline is GFP; the portion marked with a double underline is the biotin acceptor peptide; the portion marked with a dotted underline is the histidine tag; the portions enclosed with boxes are linkers; and the portions without any marking represent the rod domain of α-actinin.

FIG. 7 is a schematic diagram showing the structure of a spacer module.

FIG. 8 shows an electrophoretic gel pattern of a spacer module purified with Ni beads (Panel A) and a diagram showing the results of an experiment examining the reactivity between a spacer module purified with Ni beads and streptavidin (Panel B).

FIG. 11 shows the intracellular localization of a spacer module-linked clathrin light chain and a spacer module-linked caveolin-1.

FIG. 14 shows the observed images by rotary shadowing of clathrin molecules (triskelion) purified from a spacer module-linked clathrin light-chain expressing HEK cells using the module. Arrow marks in this Figure indicate the GFP of the spacer module. Although short type ("short" in the Figure) and long type ("long" in the Figure) spacer modules are different in length, both modules protrudes from the center of the molecule, indicating the localization of the other end of modules therein.

FIG. 15 shows the observed images by negative staining of coated vesicles purified from a spacer module-fused clathrin light-chain expressing HEK cells. Most of the particles seen under low-magnification (lower panel) are coated vesicles. Individual particles indicated with arrow marks are enlarged in the upper panel. The inserted diagram is a schematic diagram showing molecular arrangement in the coated vesicle.

FIG. 19 shows the amino acid sequence (SEQ ID NO:12) of a fusion protein comprising the rod domains of two polypeptide chains of α-actinin, a histidine tag, a biotin acceptor peptide and GFP. The portion marked with a single underline is GFP; the portion marked with a double underline is the biotin acceptor peptide; the portion marked with a dotted underline is the histidine tag; the portions enclosed with boxes are linkers; and the portions without any marking represent the rod domains of α-actinin.

FIGURE LEGENDS

Figure 9:
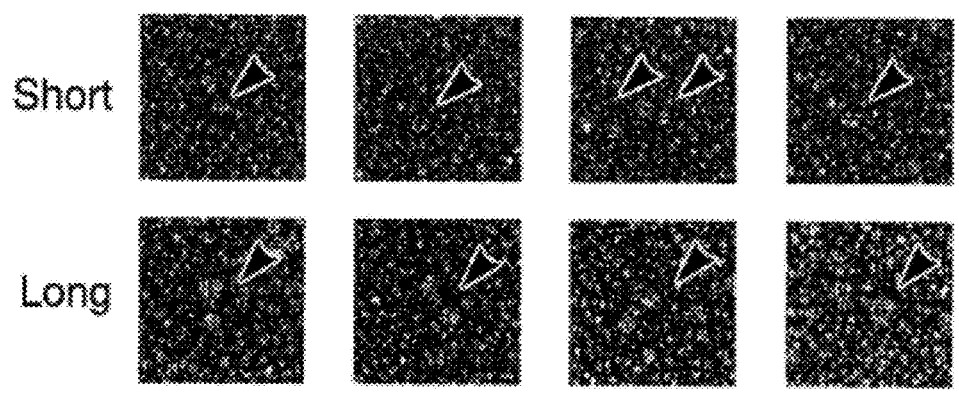
FIG. 9 shows the results of observation of spacer modules by rotary shadowing. Arrow marks in this Figure indicate spacer modules.
Figure 10:
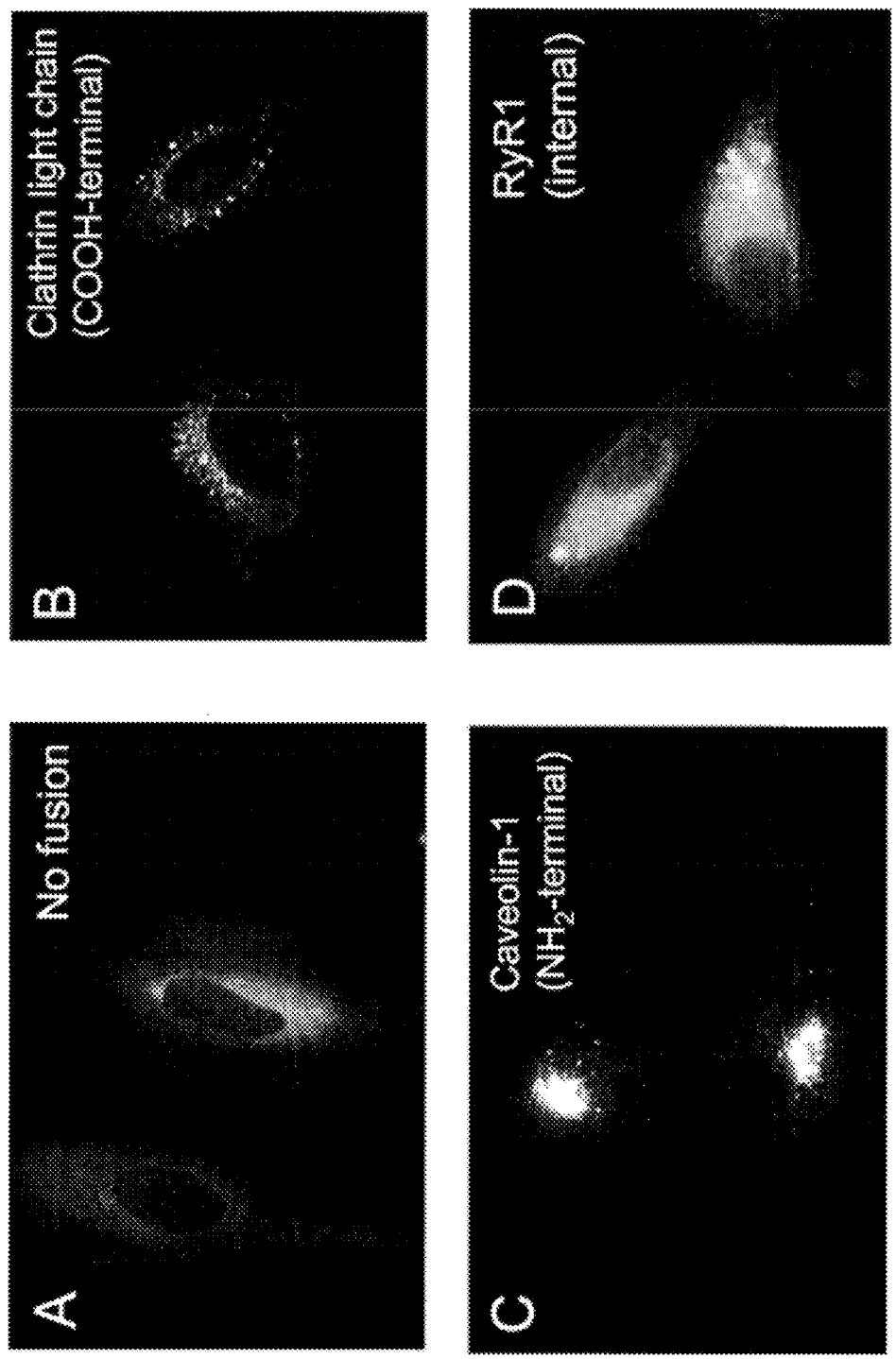
FIG. 10 shows the intracellular localization of spacer module-linked fusion proteins.

1. Tag
2. Labeling substance
3. Rod-like spacer substance
4. Interacting substance
5. Target compound
6. Protein body

BEST MODE FOR CARRYING OUT THE INVENTION

Hereinbelow, the present invention will be described in detail.

The molecular module of the present invention binds to a target compound and is used for purifying or labeling the compound. The molecular module of the present invention has a rod-like spacer substance, an interacting substance that interacts with the target compound, a tag and a labeling substance, wherein the interacting substance is positioned at one end of the rod-like spacer substance, and the tag and the labeling substance are positioned at the other end of the rod-like spacer substance.

The target compound is not particularly limited as long as the compound is capable of being purified or labeled by the molecular module of the present invention. Biopolymers such as protein or nucleic acid, or low molecular weight compounds binding thereto may be used widely.

The rod-like spacer substance is not particularly limited as long as the substance can take a rod-like spacer structure. Preferably, the rod-like spacer substance is a protein. Preferable examples include, but are not limited to, a protein taking an antiparallel coiled coil structure, a protein taking a spectrin repeat structure, a filamentous phage and a filamentous protein of a phage. As the protein taking an antiparallel coiled coil structure, for example, the stalk domain of dynein (a motor protein) or a protein based on the stalk domain of dynein to which an artificial mutation has been added in order to stabilize the antiparallel coiled coil structure may be given. Examples of such artificial mutation-added proteins include a protein consisting of a peptide represented by the amino acid sequence of SEQ ID NO: 6 and a peptide represented by the amino acid sequence of SEQ ID NO: 7 (short type) and a protein consisting of a peptide represented by the amino acid sequence of SEQ ID NO: 8 and a peptide represented by the amino acid sequence of SEQ ID NO: 9 (long type). In these examples, the length of the long type rod-like spacer structure is 150% of the length of the short type rod-like spacer structure. In addition to the above-listed examples, antiparallel coiled coil structures may be prepared based on the disclosure in Current Opinion in Structural Biology 2001, 11:450-457 and so forth. As the protein taking a spectrin repeat structure, for example, the rod domain of α-actinin or a protein based on the rod domain of α-actinin into which an artificial mutation has been added to stabilize the spectrin repeat structure may be given. Examples of the rod domain of α-actinin include a protein represented by the amino acid sequence of SEQ ID NO: 10 and a protein consisting of a peptide represented by the amino acid sequence of SEQ ID NO: 13 and a peptide represented by the amino acid sequence of SEQ ID NO: 14. In the latter protein consisting of two peptides, the labeling substance or the like is inserted between the two peptides. Examples of filamentous phage include fl phage, fd phage and M13 phage. The rod-like spacer substance may be a substance other than protein. Examples of such non-proteinaceous substances include, but are not limited to, carbon nanotube, carbon nanohorn and amylose.

The length and the diameter of rod-like spacer substance are not particularly limited as long as an appropriate distance can be secured between the target compound and the tag/the label. The length is preferably 5-50 nm, more preferably 10-30 nm. The diameter is preferably 1-10 nm, more preferably 2-5 nm.

The interacting substance may be any substance as long as it interacts with the target substance. Proteins and low molecular weight ligands may be given. The interacting substance may be selected depending on the type of the target compound. For example, when the target compound is a protein, the interacting substance may be an antibody that recognizes the protein; when the target compound is an antibody, the interacting substance may be an antigen that the antibody recognizes; when the target compound is a receptor, the interacting substance may be a ligand for the receptor; and when the target compound is a ligand, the interacting substance may be a receptor for the ligand.

The tag may be a conventional tag used in protein purification. Specific examples of such tag include, but are not limited to, histidine tags, biotin acceptor peptides (e.g., a peptide represented by the amino acid sequence of SEQ ID NO: 11), polyarginine and FK506 binding protein (FKBP). One or more tags may be used in the molecular module. When the target compound is a protein, the tag may be inserted into the protein. The site of tag insertion is not particularly limited as long as the insertion does not impair the function of the protein used as a target compound. When the protein takes a loop structure, it is preferable to insert the tag into the loop. The insertion site in a loop structure may be, for example, between amino acid residues 173 and 174 of GFP or between amino acid residues 170 and 171 of DsRed.

The labeling substance may be a conventional substance generally used for labeling biomolecules. Examples of such labeling substance include, but are not limited to, fluorescent substances, dyes, heavy metal compounds, heavy metal colloids and oxidoreductases. Preferably, the labeling substance is proteinaceous. More preferably, a fluorescent protein is used. As a preferable fluorescent protein, GFP (*Aequorea victoria* green fluorescence protein) or DsRed (*Discosoma* sp. red fluorescence protein) may be given. Other then these fluorescent proteins, variants of GFP such as enhanced green fluorescence protein (EGFP), yellow fluorescence protein (YFP), enhanced yellow fluorescence protein (EYFP), cyan fluorescence protein (CFP), enhanced cyan fluorescence protein (ECFP), blue fluorescence protein (BFP) and enhanced blue fluorescence protein (EBFP), as well as variants of DsRed such as monomeric Banana yellow fluorescence protein (mBanana), monomeric Orange fluorescence protein (mOrange), monomeric Tangerine fluorescence protein (mTangerine), monomeric Strawberry red fluorescence protein (mStrawberry) and monomeric Cherry red fluorescence protein (mCherry) may also be used. Alternatively, a non-proteinaceous fluorescent substance may be used as a labeling substance. For example, fluorescein, Rhodamine, eosin or NBD fluorescent substances, or the like may be used. Specific examples include, but are not limited to, fluorescein-5-isothiocyanate, diacyl (such as isobutyryl, acetyl or pivaloyl) fluorescein-5 and/or 6-carboxylic acid pentafluorophenyl ester, 6-(diacyl-5 and/or 6-carboxamide-fluorescein)aminohexanoic acid pentafluorophenyl ester, Texas Red (Trademark of Molecular Probes, Inc.), tetramethylrhodamine-5 (and 6) isothiocyanate, oesin-isothiocyanate, erythrosin-5-isothiocyanate, 4-chloro-7-nitrobenz-2-oxa-1,3-diazole, 4-fluoro-7-nitrobenz-2-oxa-1,3-diazol, 3-(7-nitrobenz-2-oxa-1,3-diazol-4-yl)methylaminopropionitrile, 6-(7-nitrobenz-2-oxa-1,3-diazol-4-yl-aminohexanoic acid, succinimidyl 12-(N-methyl-N-(7-nitrobenz-2-oxa-1,3-diazol-4-yl) aminododecanoate, 7-diethylamino-3-(4'-isothiocyanatophenyl)-4-methylcoumarin (CP), 7-hydroxycoumarin-4-acetic acid, 7-dimethylaminocoumarin-4-acetic acid, succinimidyl 7-dimethylaminocoumarin-4-acetate, 7-methoxycoumarin-4-acetic acid, 4-acetamide-4'-isothiocyanatostilbene-2-2'-disulfonic acid (SITS), 9-chloroacridine, succinimidyl 3-(9-carbazole)propionate, succinimidyl 1-pyrenebutyrate, succinimidyl 1-pyrenenonanoate, p-nitrophenyl 1-pyrenebutyrate, 9-anthracenepropionic acid, succinimidyl anthracene-9-propionate and 2-anthracenesulfonyl chloride.

The three members of the molecular module of rod-like spacer substance, tag and labeling substance may be in the form of a fusion protein consisting of one polypeptide chain. In this case, when the interacting substance is a low molecular weight ligand, this substance may be covalently bonded through an active group located at the end of the rod-like spacer substance (e.g., α-amino group of N-terminal amino acid, carboxyl group of C-terminal amino acid, or thiol group of cystein residue). When the interacting substance is a protein, it is also possible to prepare a fusion protein of four members including the interacting substance.

The molecular module of the present invention is used for purifying and labeling a target compound. Specifically, the molecular module may be used for the following purposes.

(1) Purification of Biological Components

When the molecular module of the present invention is added to a crude extract from a biological component, one end of the molecular module specifically binds to the biological component of interest to thereby form a complex. This complex may be recovered with resin beads or magnetic beads through the tag in the module. At the time of recovery, the target for purification may be purified alone or as the complex, or even as a still larger substance (such as intracellular organelle or cell as a whole) by adding to the solution salts or surfactants as the purpose demands.

(2) Labeling at the Time of Microscopic Observation

By using a fluorescent substance as the labeling substance, microscopic observation of fluorescence signals makes it possible to indicate the localization of the target compound in cells or intracellular organelles or to trace the kinetics of the target compound in vivo. Further, by immunoelectron microscopy using an appropriate gold colloid that binds to the tag, it is also possible to explore the ligand binding site in tissue samples. Furthermore, since the molecular module of the present invention has a unique shape with a spherical portion at the end of its rod, it is believed possible to show the binding domain in protein molecules or complexes directly with the use of high resolution electronmicroscopic images.

The positional arrangement of a rod-like spacer substance, an interacting substance, a tag and a labeling substance is, for example, as shown in FIG. 1 (A). The interacting substance [4] is positioned at one end of the rod-like spacer substance [3], and the tag [1] and the labeling substance [2] are positioned at the other end. Although the tag [1] is binding to the labeling substance [2] in this Figure, the tag may be binding to the rod-like spacer substance [3] directly. Alternatively, other arrangement opposite to this Figure may be taken in which the tag [1] is binding to the rod-like spacer substance [3] directly and the labeling substance [2] is binding to the tag [1]. With such arrangements, it is possible to retain a specific distance between the target compound [5] and the tag [1]/the labeling substance [2], which leads to elimination of various adverse effects resulting from the neighboring of these substances.

The tag and label-fused protein of the present invention has a protein body, a rod-like spacer substance, a tag and a labeling substance, wherein the protein body is positioned at one end of the rod-like spacer substance, and the tag and the labeling substance are positioned at the other end of the rod-like spacer substance.

The rod-like spacer substance, the tag and the labeling substance of the tag and label-fused protein of the present invention may be the same as those substances used in the molecular module of the present invention. Further, the positional arrangement of these substances may be the same as the arrangement in the molecular module (FIG. 1 (B)). The protein body is not particularly limited. For example, a protein playing an important role in the body, such as receptor protein, may be used. All of the rod-like spacer substance, the tag and the labeling substance are preferably a protein. More preferably, these substances and the protein body form a fusion protein consisting of one polypeptide chain. Specific examples of such fusion proteins are given in FIGS. 2 to 6 (SEQ ID NOs:1-5) and FIG. 19 (SEQ ID NO:12) (however, the protein body is not included therein). FIG. 2 shows the amino acid sequence (SEQ ID NO:1) of a fusion protein in which a protein based on the stalk domain of dynein having a mutation introduced thereinto (short type) is used as a rod-like spacer substance; a histidine tag and a biotin acceptor peptide are used as tags; and GFP is used as a labeling substance. FIG. 3 shows the amino acid sequence (SEQ ID NO:2) of a fusion protein in which a protein based on the stalk domain of dynein having a mutation introduced thereinto (short type) is used as a rod-like spacer substance; a histidine tag and a biotin acceptor peptide are used as tags; and DsRed is used as a labeling substance. FIG. 4 shows the amino acid sequence (SEQ ID NO:3) of a fusion protein in which a protein used as a rod-like spacer substance; a histidine tag and a biotin acceptor peptide are used as tags; and GFP is used as a labeling substance. FIG. 5 shows the amino acid sequence (SEQ ID NO:4) of a fusion protein in which a protein based on the stalk domain of dynein having a mutation introduced thereinto (long type) is used as a rod-like spacer substance; a histidine tag and a biotin acceptor peptide are used as tags; and DsRed is used as a labeling substance. FIG. 6 shows the amino acid sequence (SEQ ID NO:5) of a fusion protein in which the rod domain of one polypeptide chain of α-actinin is used as a rod-like spacer substance; a histidine tag and a biotin acceptor peptide are used as tags; and GFP is used as a labeling substance. FIG. 19 shows the amino acid sequence (SEQ ID NO:12) of a fusion protein in which the rod domains of two polypeptide chains of α-actinin are used as a rod-like spacer substance; a histidine tag and a biotin acceptor peptide are used as tags; and GFP is used as a labeling substance. The amino acid sequences as shown in FIG. 2, FIG. 3, FIG. 4, FIG. 5, FIG. 6 and FIG. 19 are also shown in SEQ ID NOS: 1, 2, 3, 4, 5 and 12, respectively.

The method of protein purification of the present invention is characterized by comprising the following steps: (i) a step of expressing a fusion protein-encoding DNA in a cell, wherein the fusion protein has a protein body, a rod-like spacer substance, a tag and a labeling substance, the protein body being positioned at one end of the rod-like spacer substance, and the tag and the labeling substance being positioned at the other end of the rod-like spacer substance; (ii) a step to homogenize the cell and contacting the resultant homogenate with a substance having affinity to the tag; and (iii) a step of collecting the fusion protein bound to the substance having affinity to the tag.

This method of protein purification is one application of the tag and label-fused protein of the present invention. It should be noted here that this method may be performed in the same manner as conventional purification methods for tagged proteins except that a tag and a labeling protein are added through a rod-like spacer protein.

EXAMPLES

Hereinbelow, the present invention will be described more specifically with reference to the following Examples.

Example 1

Design of Spacer Modules

Proteins consisting of the amino acid sequences as shown in FIG. 2 (SEQ ID NO:1) and FIG. 4 (SEQ ID NO:3), respectively, were designed (hereinafter, these proteins are called "spacer modules"). The spacer module has GFP, a histidine tag (8×His), a biotin acceptor peptide (biotin acceptor domain; BAD) and a protein taking an antiparallel coiled coil structure. FIG. 7 shows a schematic diagram of the structure of this spacer module. His-tag and a biotin acceptor domain are inserted into the loop domain of GFP (173-174); a protein taking an antiparallel coiled coil structure is added to the N-terminus and the C-terminus of GFP. The protein taking an antiparallel coiled coil structure is based on the stalk domain of cytoplasmic dynein. In order to improve stability, an artificial mutation has been introduced into the stalk domain. The protein taking an antiparallel coiled coil structure is different between the spacer module shown in FIG. 2 (SEQ ID NO:1) and the spacer module shown in FIG. 4 (SEQ ID NO:3). The former uses a short type rod-like spacer structure, and the latter uses a long type rod-like spacer structure.

Further, similar spacer modules were also designed using DsRed instead of GFP (FIG. 3 and FIG. 5) (SEQ ID NO:2 and SEQ ID NO:4, respectively).

Example 2

Purification of Spacer Modules with Ni Beads cDNA fragments encoding the four types of spacer modules designed in Example 1 were inserted into pCold vectors separately and allowed mass expression in *Escherichia coli* (GFP-short, DsRed-short, GFP-long and DsRed-long). The cells were homogenized, and the supernatant was bound to Ni beads. The resultant beads were washed with a solution containing 20 mM imidazole and eluted with 300 mM imidazole. The eluted fraction was subjected to SDS-PAGE. The results are shown in FIG. 8A.

Since every spacer module was detected as a single band, it was demonstrated that the histidine tag is functioning as a tag for purification. It was predicted that the rod-like portion of the short type spacer module is 16 nm long, and that portion of the long type spacer module is 24 nm long.

Example 3

Detection of Biotinylation with Streptavidin HRP

After SDS polyacrylamide-gel electrophoresis, the spacer modules purified with Ni beads were transferred onto a PVDF membrane, followed by blotting with streptavidin HRP. The results are shown in FIG. 8B.

Every spacer module reacted with streptavidin, showing that every spacer module was biotinylated.

Example 4

Observation of Morphology of Spacer Modules by Rotary Shadowing

The cDNA fragment encoding each of the above-described spacer modules was inserted into pCold TF vector and expressed as a fusion protein with trigger factor (an *E. coli* protein). The fusion protein was purified and observed by rotary shadowing. The results are shown in FIG. 9.

Both short type and long type spacer modules showed a dumbbell-like structure. The rod-like portion between spherical structures was longer in long type spacer modules. This is consistent with the above-mentioned prediction.

Example 5

Intracellular Localization of Spacer Module-Fused Proteins

Spacer module (GFP-short), alone or in the form of fusion proteins with other proteins, was expressed in HeLa cells, followed by detection of the intracellular GFP fluorescence. Micrographs showing the intracellular localization of the spacer module when expressed alone, when expressed as a fusion protein with a clathrin light chain (C-terminal fusion), when expressed as a fusion protein with caveolin-1 (N-terminal fusion) and when expressed as a fusion protein with ryanodine receptor 1 (RyR1) (internal insertion, 1379-1380) are given in FIG. 10A, FIG. 10B, FIG. 10C and FIG. 10D, respectively.

When the spacer module was expressed alone, the spacer module was evenly dispersed within the cell other than the nucleus. When expressed as a fusion protein with a clathrin light chain or caveolin-1, the spacer module was localized as dots around the nucleus and in the cytoplasm. When expressed as a fusion protein with RyR1, the spacer module was localized in a mesh-like manner within the cell, which is consistent that the spacer module was present in endoplasmic reticulum. In any of the fusion proteins tested, the localization pattern was consistent with the endogenous protein. Thus, it was suggested that the spacer module does not affect the structure or function of a protein when fused thereto.

Example 6

Double Staining with Different Spacer Modules

A fusion protein in which GFP-short is fused to the C-terminus of a clathrin light chain and a fusion protein in which DsRed-short is fused to the N-terminus of caveolin-1 were expressed in HeLa cells, followed by observation of cells expressing both proteins. The results are shown in FIG. 11.

Although both fusion proteins were localized in dotted manner around the nucleus and in the cytoplasm, their distributions were different from each other.

Example 7

Example of Purification of Spacer Module-Fused Protein Expressed in Mammalian Cell (Part 1)

Figure 12:
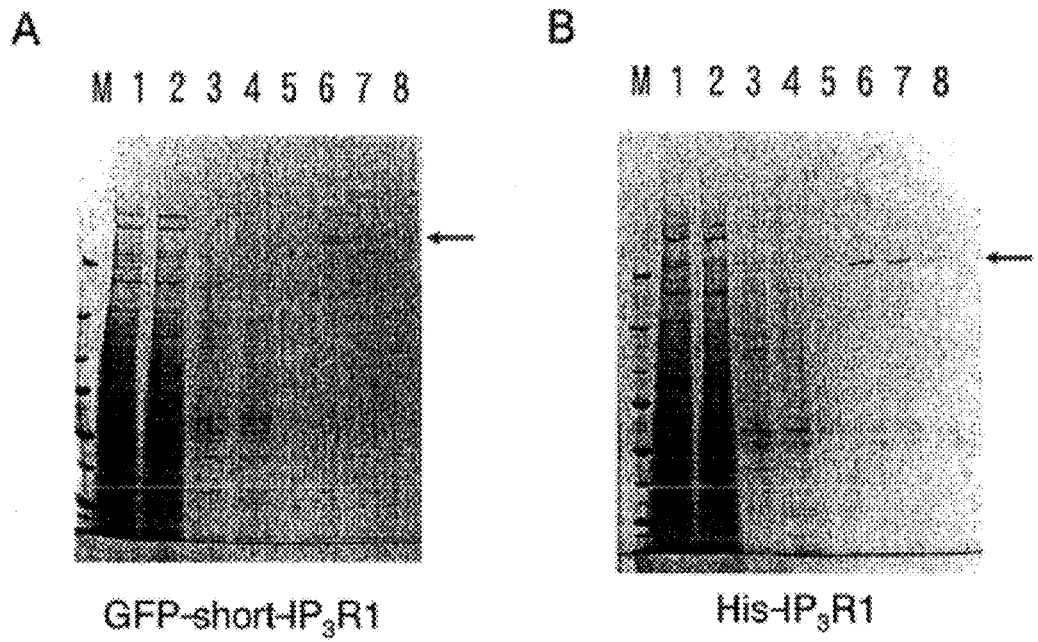
FIG. 12 shows electrophoretic gel pattern of fractions obtained from individual purification steps when a fusion protein of a spacer module and IP3R1 was purified with an Ni column. Panel A shows the results for a spacer module-fused IP3R1. Panel B shows the results for a His tag-added IP3R1. Lane 1: sample applied to the column; lane 2: those which passed through the column; lane 3: first washed fraction; lane 4: second washed fraction; lanes 5 to 8: eluted fractions.

A DNA fragment encoding a fusion protein of GFP-short and IP3R1 (N-terminal fusion) was introduced into Flp-In T-REx HEK cells, followed by selection of cell clones expressing the fusion protein stably. After induction of expression with doxycycline, membrane fractions were prepared. IP3R1 was solubilized with CHAPS and applied to an Ni column. The column was washed with 100 mM imidazole, followed by elution with 300 mM imidazole. The proteins included in fractions from individual purification stages were separated by electrophoresis. For the purpose of comparison, IP3R1 to which a histidine tag had been added at its N-terminus was also expressed in the same manner, and the proteins included in fractions of individual purification stages were examined in the same manner. The results are shown in FIG. 12.

Since the spacer module fused protein was purified in the same manner as the histidine tag-inserted IP3R1 (N-terminus), it was revealed that the spacer module functions as a tag for purification.

Example 8

Example of Purification of Spacer Module-Fused Protein Expressed in Mammalian Cell (Part 2)

Figure 13:
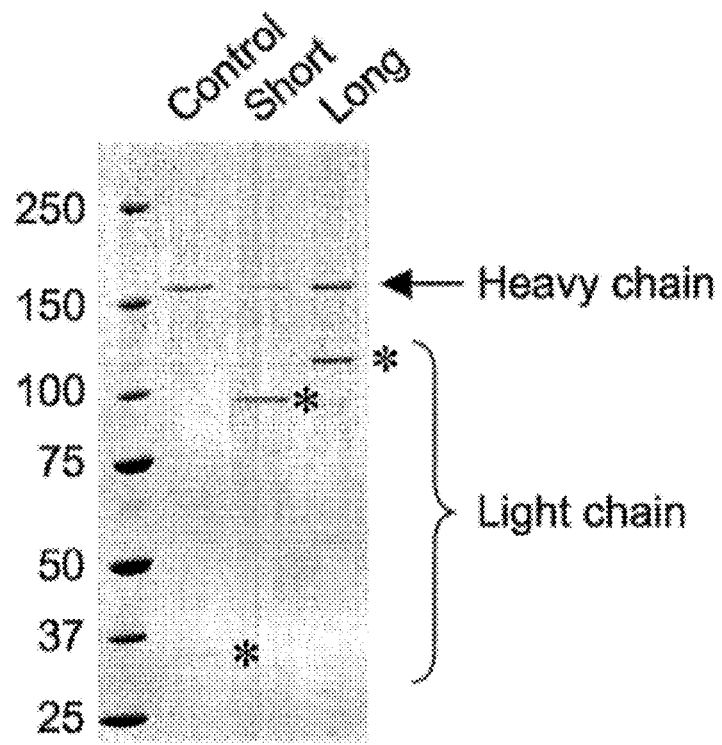
FIG. 13 shows an electrophoretic gel pattern obtained when an extract from HEK cells was purified with a Ni column, wherein the HEK cells express clathrin light chain to which a spacer module was linked at its C terminus. In the control, a histidine tag was added instead of a spacer module.

A DNA fragment encoding a fusion protein of GFP-short or GFP-long and a clathrin light chain (C-terminal fusion) was introduced into Flp-In T-REx HEK cells, followed by selection of cell clones expressing the fusion protein stably. After induction of expression with doxycycline, membrane fractions were prepared. Triskelion was extracted with 0.5 M NaCl and applied to a Ni column. The column was washed with 100 mM imidazole, followed by elution with 300 mM imidazole. The proteins contained in the 300 mM imidazole elution fraction were detected by electrophoresis. As a control, a clathrin light chain to which a histidine tag had been added at its C-terminus was expressed. The results are shown in FIG. 13.

Since a clathrin heavy chain of 160 kDa was purified together with the spacer module-fused clathrin light chain, it was revealed that clathrin was purified as a protein complex.

Example 9

Observation of Morphology of Spacer Module-Fused Clathrin Complexes by Rotary Shadowing The clathrin complexes purified in Example 8 were observed by rotary shadowing.

The clathrin complex into which a histidine tag had been inserted at the C-terminus showed a typical triskelion structure. In the short type spacer module-fused clathrin light chain, a spherical structure corresponding to GFP was observed at a site slightly away from the center of triskelion corresponding to the C-terminus of the clathrin light chain. In the long type spacer module-fused clathrin light chain, the spherical structure corresponding to GFP and even the rod-like portion were observed at sites further away from the center of triskelion. Thus, the localization of the spacer module in the protein complexes could be confirmed.

Example 10

Example of Purification of Intracellular Organelles from spacer Module-Fused Protein Expressing Cells A DNA fragment encoding a fusion protein of a spacer module (GFP which comprises a histidine tag and a biotin acceptor sequence and is flanked by TEV protease site on both sides) and a clathrin light chain (C-terminal fusion) was introduced into Flp-In T-REx HEK cells, followed by selection of cell clones expressing the fusion protein stably. After induction of expression with doxycycline, cells were homogenized in a solution containing 0.1 M MES, pH 6.5, 0.5 mM $MgCl_2$ and 1 mM EGTA, followed by preparation of membrane fractions. The resultant membrane fraction was bound to streptavidin magnetic beads, washed with the above-described buffer solution and then treated with TEV protease at room temperature for 1 hr. Eluted fractions were observed with electron microscopy after negative staining. The results are shown in FIG. 15.

A great number of vesicles approximately 100 nm in diameter were observed in the eluted fraction. When enlarged, the vesicles were surrounded by soccer ball-like skeletons. It was confirmed that these vesicles represent the morphology of a typical clathrin coated vesicle.

Example 11

Figure 16:
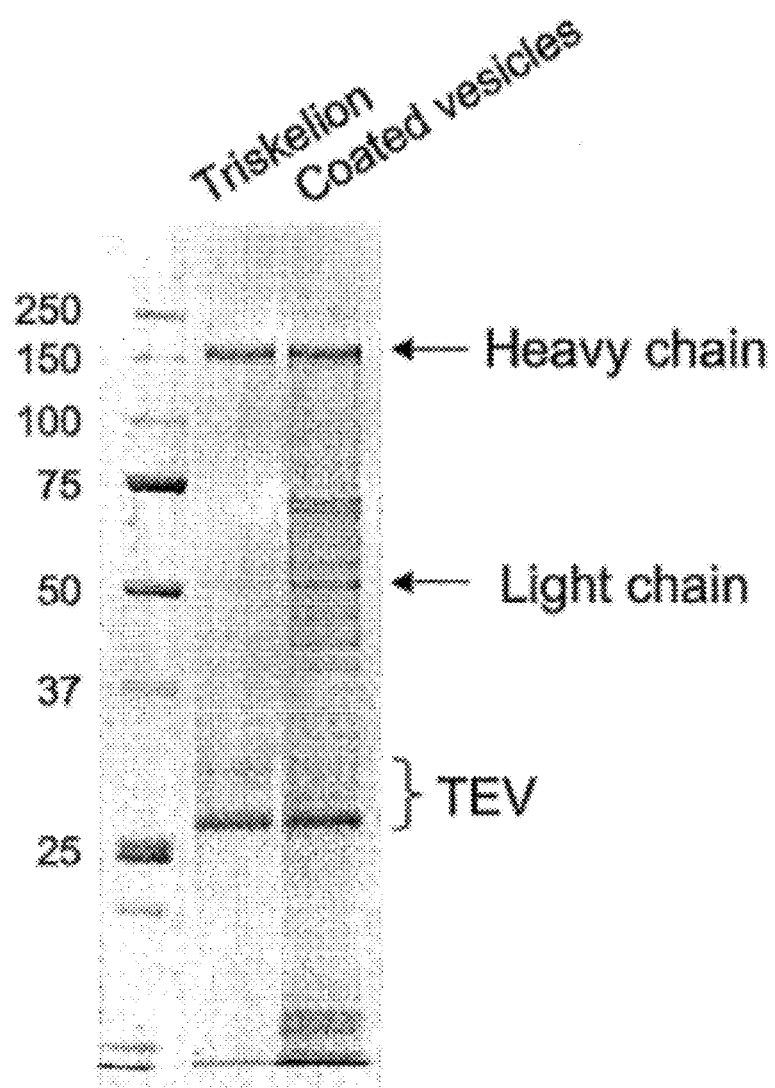
FIG. 16 shows an (electrophoretic gel pattern?) of coated vesicles purified from a spacer module-fused clathrin light chain expressing HEK cells (right lane). The central lane represents clathrin molecules (triskelion) which were purified alone after solubilization. The left lane represents molecular weight marker. The fraction purified as coated vesicles contains a large number of component proteins other than clathrin.

Example of Purification of Intracellular Organelles Comprising Spacer Module-Fused Protein Expressed in Mammalian Cell The proteins included in the coated vesicle fraction obtained in Example 10 were separated by electrophoresis. For the purpose of comparison, triskelion obtained by extracting the above fraction with 0.5 M NaCl was purified in the same manner. The results are shown in FIG. 16.

In the coated vesicle fraction, bands of a large number of other component proteins in addition to the clathrin heavy and light chains contained in triskelion were detected. The band around 27 kDa is derived from TEV protease. It was revealed that the spacer module functions effectively as a tag for purifying intracellular organelles.

Example 12

Intracellular Localization of Spectrin Repeat Type Spacer Module-Fused Protein (Part 1)

Figure 17:
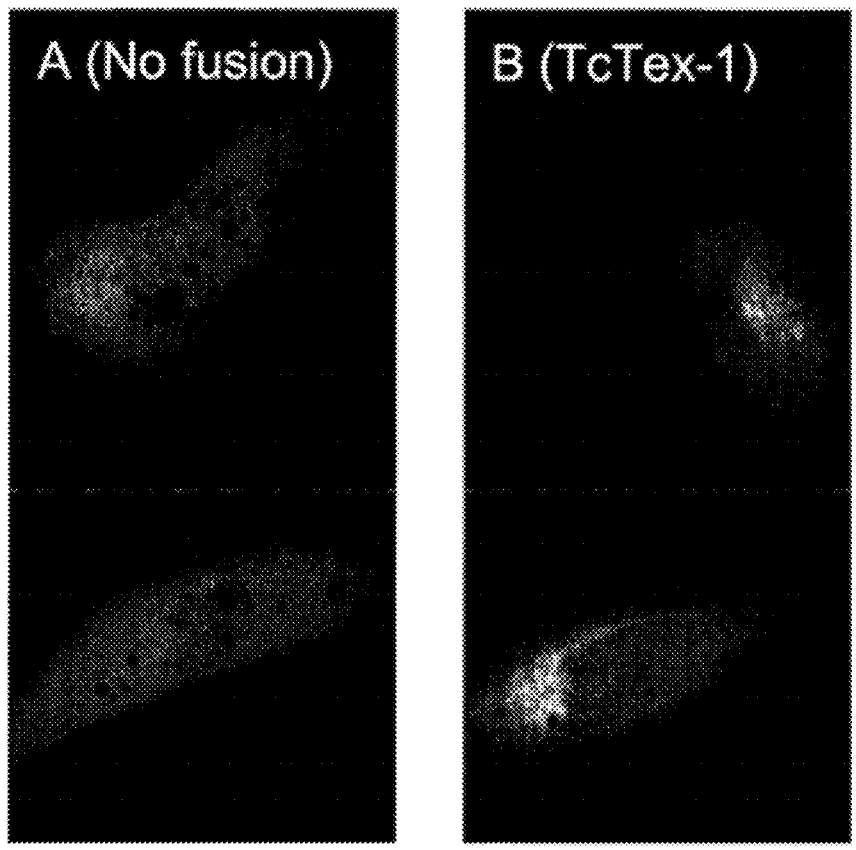
FIG. 17 shows the intracellular localization of a cytoplasmic dynein light chain linked to a spectrin repeat type spacer module. Panel A shows the spacer module alone, and Panel B shows the spacer linked to cytoplasmic dynein light chain.

A spectrin repeat type spacer module (comprising a protein represented by the amino acid sequence of SEQ ID NO: 10), alone or in the form of a fusion protein with other protein, was expressed in HeLa cells, followed by detection of intracellular GFP fluorescence. Micrographs showing the intracellular localization of the spectrin repeat type spacer module when expressed alone and when expressed as a fusion protein with a cytoplasmic dynein light chain (TcTex-1) are given in FIG. 17A and FIG. 17B, respectively.

When the spectrin repeat type spacer module had been expressed alone, the spacer module was evenly dispersed within the cell except the nucleus. When the spacer module had been expressed as a fusion protein with a cytoplasmic dynein light chain, the spectrin repeat type spacer module was localized around the nucleus. Since its localization pattern was consistent with that of the endogenous protein, it was suggested that the spectrin repeat type spacer module does not affect the structure or function of a protein when fused thereto.

Example 13

Intracellular Localization of Spectrin Repeat Type Spacer Module-Fused Protein (Part 2)

Figure 18:
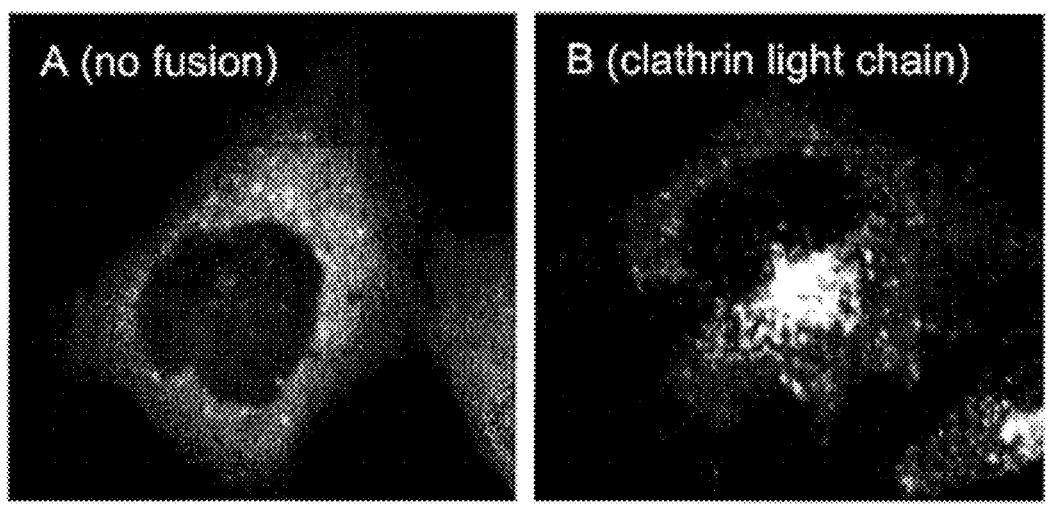
FIG. 18 shows the intracellular localization of a clathrin light chain fused to a spectrin repeat type spacer module. While no localization at a specific site is observed when the spacer module was expressed alone (Panel A), localization equivalent to that of wild-type clathrin was observed when the spacer module was fused to the clathrin light chain (Panel B).

A spectrin repeat type spacer module (comprising a peptide represented by the amino acid sequence of SEQ ID NO: 13 and a peptide represented by the amino acid sequence of SEQ ID NO: 14), alone or in the form of a fusion protein with other protein, was expressed in HeLa cells, followed by detection of intracellular GFP fluorescence. Micrographs showing the intracellular localization of the spectrin repeat type spacer module when expressed alone and when expressed as a fusion protein with a clathrin light chain are given in FIG. 18A and FIG. 18B, respectively.

When the spectrin repeat type spacer module had been expressed alone, the spacer module was evenly dispersed within the cell except the nucleus. When the spacer module had been expressed as a fusion protein with a clathrin light chain, the spectrin repeat type spacer module was localized in a dot-like manner around the nucleus and in the cytoplasm. It was suggested that the spectrin repeat type spacer module does not affect the structure or function of a protein when fused thereto.

The present specification encompasses the disclosure of the specification and/or drawings of Japanese Patent Application No. 2006-332530 based on which the present patent application claims priority. All publications, patents and patent applications cited herein are incorporated herein by reference in their entirety.

The invention claimed is:

1. A labeled fusion protein comprising a first protein, a rod-like spacer, a tag and a label, wherein the first protein is positioned at one end of the rod-like spacer, and the tag and the label are positioned at the other end of the rod-like spacer, wherein the rod-like spacer is a protein that has an antiparallel coiled coil structure and is composed of a first rod-like spacer domain and a second-rod like spacer domain, wherein the tag is an isolation tag for purification of the fusion protein and the label is for detecting the fusion protein, wherein the tag and label are located between the first rod-like spacer domain and the second rod-like spacer domain, and wherein the first protein, the rod-like spacer, the tag and the label form a polypeptide chain.

2. The labeled fusion protein according to claim 1, wherein the rod-like spacer is a protein that has a spectrin repeat structure.

3. The labeled fusion protein according to claim 2, wherein the tag is a histidine tag or a biotin acceptor peptide.

4. The labeled fusion protein according to claim 2, wherein the label is GFP or DsRed.

5. The labeled fusion protein according to claim 1, wherein the tag is a histidine tag or a biotin acceptor peptide.

6. The labeled fusion protein according to claim 5, wherein the label is GFP or DsRed.

7. The labeled fusion protein according to claim 1, wherein the label is GFP or DsRed.

8. A method of protein purification comprising the following steps:

(i) expressing a fusion protein-encoding DNA in a cell, wherein the fusion protein comprises a first protein, a rod-like spacer, a tag and a label, wherein the first protein is positioned at one end of the rod-like spacer, the tag and the label are positioned at the other end of the rod-like spacer, and the rod-like spacer is a protein that has an antiparallel coiled coil structure and is composed of a first rod-like spacer domain and a second-rod like spacer domain, wherein the tag is an isolation tag for purification of the fusion protein and the label is for detecting the fusion protein, wherein the tag and label are located between the first rod-like spacer domain and the second rod-like spacer domain, and wherein the first protein, the rod-like spacer, the tag and the label form a polypeptide chain;

(ii) homogenizing the cell and contacting the resultant homogenate with a target compound having affinity for the tag; and (iii) collecting the fusion protein bound to the target compound.

9. The method according to claim 8, wherein the rod-like spacer is a protein that has a spectrin repeat structure.

10. The method according to claim 8, wherein the tag is a histidine tag or a biotin acceptor peptide.

11. The method according to claim 8, wherein the label is GFP or DsRed.

* * * * *

SEQUENCE LISTING

```
<160> NUMBER OF SEQ ID NOS: 14

<210> SEQ ID NO 1
<211> LENGTH: 539
<212> TYPE: PRT
<213> ORGANISM: Artificial Sequence
<220> FEATURE:
<223> OTHER INFORMATION: Description of Artificial Sequence: fusion
      protein

<400> SEQUENCE: 1

Val Asp Gln Leu Lys Ile Lys Val Glu Gln Leu Lys Glu Lys Val Asn
  1               5                  10                  15

Glu Leu Glu Leu Glu Asn Asp Glu Leu Lys Ala Lys Val Asp Asn Leu
             20                  25                  30

Asn Ser Lys Asn Arg Glu Leu Asp Val Lys Asn Glu Gln Ala Asn Gln
         35                  40                  45

Lys Leu Lys Gln Leu Val Gln Asp Val Gln Ala Ala Glu Ile Lys Val
     50                  55                  60

Lys Asp Ala Ser Glu Leu Gln Val Gln Leu Asp Val Arg Asn Lys Glu
```

-continued

```
             65                  70                  75                  80
        Ile Ala Val Gln Lys Val Lys Ala His Ala Asp Leu Glu Lys Ala Glu
                         85                  90                  95

Pro Ala Ile Ile Glu Gly Ser Gly Val Ser Lys Gly Glu Glu Leu Phe
                        100                 105                 110

Thr Gly Val Val Pro Ile Leu Val Glu Leu Asp Gly Asp Val Asn Gly
                        115                 120                 125

His Lys Phe Ser Val Ser Gly Glu Gly Glu Gly Asp Ala Thr Tyr Gly
                        130                 135                 140

Lys Leu Thr Leu Lys Phe Ile Cys Thr Thr Gly Lys Leu Pro Val Pro
        145                 150                 155                 160

Trp Pro Thr Leu Val Thr Thr Leu Thr Tyr Gly Val Gln Cys Phe Ser
                        165                 170                 175

Arg Tyr Pro Asp His Met Lys Gln His Asp Phe Phe Lys Ser Ala Met
                        180                 185                 190

Pro Glu Gly Tyr Val Gln Glu Arg Thr Ile Phe Phe Lys Asp Asp Gly
                        195                 200                 205

Asn Tyr Lys Thr Arg Ala Glu Val Lys Phe Glu Gly Asp Thr Leu Val
                        210                 215                 220

Asn Arg Ile Glu Leu Lys Gly Ile Asp Phe Lys Glu Asp Gly Asn Ile
        225                 230                 235                 240

Leu Gly His Lys Leu Glu Tyr Asn Tyr Asn Ser His Asn Val Tyr Ile
                        245                 250                 255

Met Ala Asp Lys Gln Lys Asn Gly Ile Lys Val Asn Phe Lys Ile Arg
                        260                 265                 270

His Asn Ile Glu Asp Gly Ser Gly His His His His His His
                        275                 280                 285

Gly Ser Gly Ala Gly Thr Pro Val Thr Ala Pro Leu Ala Gly Thr Ile
                        290                 295                 300

Trp Lys Val Leu Ala Ser Glu Gly Gln Thr Val Ala Ala Gly Glu Val
        305                 310                 315                 320

Leu Leu Ile Leu Glu Ala Met Lys Met Glu Thr Glu Ile Arg Ala Ala
                        325                 330                 335

Gln Ala Gly Thr Val Arg Gly Ile Ala Val Lys Ala Gly Asp Ala Val
                        340                 345                 350

Ala Val Gly Asp Thr Leu Met Thr Leu Ala Gly Ser Gly Ser His Gly
                        355                 360                 365

Ser Gly Ser Val Gln Leu Ala Asp His Tyr Gln Gln Asn Thr Pro Ile
                        370                 375                 380

Gly Asp Gly Pro Val Leu Leu Pro Asp Asn His Tyr Leu Ser Thr Gln
        385                 390                 395                 400

Ser Ala Leu Ser Lys Asp Pro Asn Glu Lys Arg Asp His Met Val Leu
                        405                 410                 415

Leu Glu Phe Val Thr Ala Ala Gly Ile Thr Leu Gly Met Asp Glu Leu
                        420                 425                 430

Tyr Lys Gly Ser Gly Ser Glu Ile Leu Asp Arg Ile Lys Pro Leu Arg
                        435                 440                 445

Glu Glu Val Glu Gln Leu Glu Asn Ala Ala Asn Glu Leu Lys Leu Lys
                        450                 455                 460

Gln Asp Glu Ile Val Ala Thr Ile Thr Ala Leu Glu Lys Ser Ile Ala
        465                 470                 475                 480

Ser Leu Lys Glu Glu Val Ala Thr Leu Ile Arg Glu Thr Glu Gln Ile
                        485                 490                 495
```

```
Lys Thr Glu Ser Ser Lys Val Lys Ala Gln Val Gln Ala Leu Glu Ile
            500                 505                 510

Glu Val Lys Asp Asn Lys Thr Lys Val Val Gln Leu Glu Val Glu Val
            515                 520                 525

Ala Gln Leu Glu Ser Glu Val Lys Asp Leu Glu
            530                 535

<210> SEQ ID NO 2
<211> LENGTH: 519
<212> TYPE: PRT
<213> ORGANISM: Artificial Sequence
<220> FEATURE:
<223> OTHER INFORMATION: Description of Artificial Sequence: fusion
      protein

<400> SEQUENCE: 2

Val Asp Gln Leu Lys Ile Lys Val Glu Gln Leu Lys Glu Lys Val Asn
 1               5                  10                  15

Glu Leu Glu Leu Glu Asn Asp Glu Leu Lys Ala Lys Val Asp Asn Leu
            20                  25                  30

Asn Ser Lys Asn Arg Glu Leu Asp Val Lys Asn Glu Gln Ala Asn Gln
        35                  40                  45

Lys Leu Lys Gln Leu Val Gln Asp Val Gln Ala Ala Glu Ile Lys Val
    50                  55                  60

Lys Asp Ala Ser Glu Leu Gln Val Gln Leu Asp Val Arg Asn Lys Glu
65                  70                  75                  80

Ile Ala Val Gln Lys Val Lys Ala His Ala Asp Leu Glu Lys Ala Glu
                85                  90                  95

Pro Ala Ile Ile Glu Gly Ser Gly Asp Asn Thr Glu Asp Val Ile Lys
            100                 105                 110

Glu Phe Met Gln Phe Lys Val Arg Met Glu Gly Ser Val Asn Gly His
        115                 120                 125

Tyr Phe Glu Ile Glu Gly Glu Gly Glu Gly Lys Pro Tyr Glu Gly Thr
    130                 135                 140

Gln Thr Ala Lys Leu Gln Val Thr Lys Gly Gly Pro Leu Pro Phe Ala
145                 150                 155                 160

Trp Asp Ile Leu Ser Pro Gln Phe Gln Tyr Gly Ser Lys Ala Tyr Val
                165                 170                 175

Lys His Pro Ala Asp Ile Pro Asp Tyr Met Lys Leu Ser Phe Pro Glu
            180                 185                 190

Gly Phe Thr Trp Glu Arg Ser Met Asn Phe Glu Asp Gly Gly Val Val
        195                 200                 205

Glu Val Gln Gln Asp Ser Ser Leu Gln Asp Gly Thr Phe Ile Tyr Lys
    210                 215                 220

Val Lys Phe Lys Gly Val Asn Phe Pro Ala Asp Gly Pro Val Met Gln
225                 230                 235                 240

Lys Lys Thr Ala Gly Trp Glu Pro Ser Thr Glu Lys Leu Tyr Pro Gln
                245                 250                 255

Asp Gly Val Leu Lys Gly Glu Ile Ser His Ala Leu Lys Leu Lys Asp
            260                 265                 270

Gly Ser Gly His His His His His His Gly Ser Gly Ala Gly
        275                 280                 285

Thr Pro Val Thr Ala Pro Leu Ala Gly Thr Ile Trp Lys Val Leu Ala
    290                 295                 300

Ser Glu Gly Gln Thr Val Ala Ala Gly Glu Val Leu Leu Ile Leu Glu
305                 310                 315                 320
```

-continued

```
Ala Met Lys Met Glu Thr Glu Ile Arg Ala Ala Gln Ala Gly Thr Val
            325                 330                 335

Arg Gly Ile Ala Val Lys Ala Gly Asp Ala Val Ala Val Gly Asp Thr
        340                 345                 350

Leu Met Thr Leu Ala Gly Ser Gly Ser His Tyr Thr Cys Asp Phe Lys
        355                 360                 365

Thr Val Tyr Lys Ala Lys Lys Pro Val Gln Leu Pro Gly Asn His Tyr
    370                 375                 380

Val Asp Ser Lys Leu Asp Ile Thr Asn His Asn Glu Asp Tyr Thr Val
385                 390                 395                 400

Val Glu Gln Tyr Glu His Ala Glu Ala Arg His Ser Gly Ser Gln Ser
                405                 410                 415

Gly Ser Glu Ile Leu Asp Arg Ile Lys Pro Leu Arg Glu Glu Val Glu
            420                 425                 430

Gln Leu Glu Asn Ala Ala Asn Glu Leu Lys Leu Lys Gln Asp Glu Ile
        435                 440                 445

Val Ala Thr Ile Thr Ala Leu Glu Lys Ser Ile Ala Ser Leu Lys Glu
    450                 455                 460

Glu Val Ala Thr Leu Ile Arg Glu Thr Glu Gln Ile Lys Thr Glu Ser
465                 470                 475                 480

Ser Lys Val Lys Ala Gln Val Gln Ala Leu Glu Ile Glu Val Lys Asp
                485                 490                 495

Asn Lys Thr Lys Val Val Gln Leu Glu Val Glu Val Ala Gln Leu Glu
            500                 505                 510

Ser Glu Val Lys Asp Leu Glu
        515
```

<210> SEQ ID NO 3
<211> LENGTH: 665
<212> TYPE: PRT
<213> ORGANISM: Artificial Sequence
<220> FEATURE:
<223> OTHER INFORMATION: Description of Artificial Sequence: fusion
      protein

<400> SEQUENCE: 3

```
Val Asp Gln Leu Lys Ile Lys Val Glu Gln Leu Lys Glu Lys Val Asn
1               5                   10                  15

Glu Leu Glu Leu Glu Asn Asp Glu Leu Lys Ala Lys Val Asp Asn Leu
            20                  25                  30

Asn Ser Lys Asn Arg Glu Leu Asp Val Lys Asn Glu Gln Ala Asn Gln
        35                  40                  45

Lys Leu Lys Gln Leu Val Gln Asp Val Gln Ala Val Arg Ile Lys Ser
    50                  55                  60

Gln Glu Leu Glu Val Lys Asn Ala Ala Ala Asn Asp Lys Leu Lys Lys
65                  70                  75                  80

Met Val Lys Asp Gln Gln Glu Ala Glu Lys Lys Val Met Ser Gln
                85                  90                  95

Glu Ile Gln Glu Gln Leu His Lys Gln Gln Val Ile Ala Asp Lys
            100                 105                 110

Gln Met Ser Val Lys Glu Asp Leu Asp Lys Ala Glu Ile Lys Val Lys
        115                 120                 125

Asp Ala Ser Glu Leu Gln Val Gln Leu Asp Val Arg Asn Lys Glu Ile
    130                 135                 140

Ala Val Gln Lys Val Lys Ala His Ala Asp Leu Glu Lys Ala Glu Pro
145                 150                 155                 160
```

```
Ala Ile Ile Glu Gly Ser Gly Val Ser Lys Gly Glu Leu Phe Thr
            165                 170                 175

Gly Val Val Pro Ile Leu Val Glu Leu Asp Gly Asp Val Asn Gly His
        180                 185                 190

Lys Phe Ser Val Ser Gly Glu Gly Glu Gly Asp Ala Thr Tyr Gly Lys
            195                 200                 205

Leu Thr Leu Lys Phe Ile Cys Thr Thr Gly Lys Leu Pro Val Pro Trp
        210                 215                 220

Pro Thr Leu Val Thr Thr Leu Thr Tyr Gly Val Gln Cys Phe Ser Arg
225                 230                 235                 240

Tyr Pro Asp His Met Lys Gln His Asp Phe Phe Lys Ser Ala Met Pro
                245                 250                 255

Glu Gly Tyr Val Gln Glu Arg Thr Ile Phe Phe Lys Asp Asp Gly Asn
        260                 265                 270

Tyr Lys Thr Arg Ala Glu Val Lys Phe Glu Gly Asp Thr Leu Val Asn
            275                 280                 285

Arg Ile Glu Leu Lys Gly Ile Asp Phe Lys Glu Asp Gly Asn Ile Leu
        290                 295                 300

Gly His Lys Leu Glu Tyr Asn Tyr Asn Ser His Asn Val Tyr Ile Met
305                 310                 315                 320

Ala Asp Lys Gln Lys Asn Gly Ile Lys Val Asn Phe Lys Ile Arg His
                325                 330                 335

Asn Ile Glu Asp Gly Ser Gly His His His His His His Gly
        340                 345                 350

Ser Gly Ala Gly Thr Pro Val Thr Ala Pro Leu Ala Gly Thr Ile Trp
            355                 360                 365

Lys Val Leu Ala Ser Glu Gly Gln Thr Val Ala Ala Gly Glu Val Leu
        370                 375                 380

Leu Ile Leu Glu Ala Met Lys Met Glu Thr Glu Ile Arg Ala Ala Gln
385                 390                 395                 400

Ala Gly Thr Val Arg Gly Ile Ala Val Lys Ala Gly Asp Ala Val Ala
                405                 410                 415

Val Gly Asp Thr Leu Met Thr Leu Ala Gly Ser Gly Ser His Gly Ser
        420                 425                 430

Gly Ser Val Gln Leu Ala Asp His Tyr Gln Gln Asn Thr Pro Ile Gly
            435                 440                 445

Asp Gly Pro Val Leu Leu Pro Asp Asn His Tyr Leu Ser Thr Gln Ser
        450                 455                 460

Ala Leu Ser Lys Asp Pro Asn Glu Lys Arg Asp His Met Val Leu Leu
465                 470                 475                 480

Glu Phe Val Thr Ala Ala Gly Ile Thr Leu Gly Met Asp Glu Leu Tyr
                485                 490                 495

Lys Gly Ser Gly Ser Glu Ile Leu Asp Arg Ile Lys Pro Leu Arg Glu
        500                 505                 510

Glu Val Glu Gln Leu Glu Asn Ala Ala Asn Glu Leu Lys Leu Lys Gln
            515                 520                 525

Asp Glu Ile Val Ala Thr Ile Thr Ala Leu Glu Lys Ser Ile Ala Ser
        530                 535                 540

Leu Arg Asn Glu Leu Gln Lys Leu Glu Asp Asp Ala Lys Asp Asn Gln
545                 550                 555                 560

Gln Lys Ala Asn Glu Val Glu Gln Met Ile Arg Asp Leu Glu Ala Ser
                565                 570                 575

Ile Ala Arg Tyr Lys Glu Glu Tyr Ala Val Leu Ile Ser Glu Ala Gln
        580                 585                 590
```

```
Ala Ile Lys Ala Asp Leu Ala Ala Val Glu Ala Lys Val Lys Ser Leu
            595                 600                 605

Lys Glu Glu Val Ala Thr Leu Ile Arg Glu Thr Gln Ile Lys Thr
    610                 615                 620

Glu Ser Ser Lys Val Lys Ala Gln Val Gln Leu Glu Ile Glu Val
625                 630                 635                 640

Lys Asp Asn Lys Thr Lys Val Val Gln Leu Glu Val Glu Val Ala Gln
            645                 650                 655

Leu Glu Ser Glu Val Lys Asp Leu Glu
            660                 665

<210> SEQ ID NO 4
<211> LENGTH: 645
<212> TYPE: PRT
<213> ORGANISM: Artificial Sequence
<220> FEATURE:
<223> OTHER INFORMATION: Description of Artificial Sequence: fusion
      protein

<400> SEQUENCE: 4

Val Asp Gln Leu Lys Ile Lys Val Glu Gln Leu Lys Glu Lys Val Asn
1               5                   10                  15

Glu Leu Glu Leu Glu Asn Asp Glu Leu Lys Ala Lys Val Asp Asn Leu
            20                  25                  30

Asn Ser Lys Asn Arg Glu Leu Asp Val Lys Asn Glu Gln Ala Asn Gln
        35                  40                  45

Lys Leu Lys Gln Leu Val Gln Asp Val Gln Ala Val Arg Ile Lys Ser
    50                  55                  60

Gln Glu Leu Glu Val Lys Asn Ala Ala Ala Asn Asp Lys Leu Lys Lys
65                  70                  75                  80

Met Val Lys Asp Gln Gln Glu Ala Glu Lys Lys Lys Val Met Ser Gln
            85                  90                  95

Glu Ile Gln Glu Gln Leu His Lys Gln Gln Glu Val Ile Ala Asp Lys
            100                 105                 110

Gln Met Ser Val Lys Glu Asp Leu Asp Lys Ala Glu Ile Lys Val Lys
        115                 120                 125

Asp Ala Ser Glu Leu Gln Val Gln Leu Asp Val Arg Asn Lys Glu Ile
    130                 135                 140

Ala Val Gln Lys Val Lys Ala His Ala Asp Leu Glu Lys Ala Glu Pro
145                 150                 155                 160

Ala Ile Ile Glu Gly Ser Gly Asp Asn Thr Glu Asp Val Ile Lys Glu
            165                 170                 175

Phe Met Gln Phe Lys Val Arg Met Glu Gly Ser Val Asn Gly His Tyr
            180                 185                 190

Phe Glu Ile Glu Gly Glu Gly Glu Gly Lys Pro Tyr Glu Gly Thr Gln
        195                 200                 205

Thr Ala Lys Leu Gln Val Thr Lys Gly Gly Pro Leu Pro Phe Ala Trp
    210                 215                 220

Asp Ile Leu Ser Pro Gln Phe Gln Tyr Gly Ser Lys Ala Tyr Val Lys
225                 230                 235                 240

His Pro Ala Asp Ile Pro Asp Tyr Met Lys Leu Ser Phe Pro Glu Gly
            245                 250                 255

Phe Thr Trp Glu Arg Ser Met Asn Phe Glu Asp Gly Gly Val Val Glu
            260                 265                 270

Val Gln Gln Asp Ser Ser Leu Gln Asp Gly Thr Phe Ile Tyr Lys Val
        275                 280                 285
```

```
Lys Phe Lys Gly Val Asn Phe Pro Ala Asp Gly Pro Val Met Gln Lys
            290                 295                 300

Lys Thr Ala Gly Trp Glu Pro Ser Thr Glu Lys Leu Tyr Pro Gln Asp
305                 310                 315                 320

Gly Val Leu Lys Gly Glu Ile Ser His Ala Leu Lys Leu Lys Asp Gly
                325                 330                 335

Ser Gly His His His His His His Gly Ser Gly Ala Gly Thr
            340                 345                 350

Pro Val Thr Ala Pro Leu Ala Gly Thr Ile Trp Lys Val Leu Ala Ser
            355                 360                 365

Glu Gly Gln Thr Val Ala Ala Gly Glu Val Leu Leu Ile Leu Glu Ala
            370                 375                 380

Met Lys Met Glu Thr Glu Ile Arg Ala Ala Gln Ala Gly Thr Val Arg
385                 390                 395                 400

Gly Ile Ala Val Lys Ala Gly Asp Ala Val Ala Val Gly Asp Thr Leu
                405                 410                 415

Met Thr Leu Ala Gly Ser Gly Ser His Tyr Thr Cys Asp Phe Lys Thr
            420                 425                 430

Val Tyr Lys Ala Lys Lys Pro Val Gln Leu Pro Gly Asn His Tyr Val
            435                 440                 445

Asp Ser Lys Leu Asp Ile Thr Asn His Asn Glu Asp Tyr Thr Val Val
450                 455                 460

Glu Gln Tyr Glu His Ala Glu Ala Arg His Ser Gly Ser Gln Ser Gly
465                 470                 475                 480

Ser Glu Ile Leu Asp Arg Ile Lys Pro Leu Arg Glu Val Glu Gln
                485                 490                 495

Leu Glu Asn Ala Ala Asn Glu Leu Lys Leu Lys Gln Asp Glu Ile Val
            500                 505                 510

Ala Thr Ile Thr Ala Leu Glu Lys Ser Ile Ala Ser Leu Arg Asn Glu
            515                 520                 525

Leu Gln Lys Leu Glu Asp Asp Ala Lys Asp Asn Gln Lys Ala Asn
            530                 535                 540

Glu Val Glu Gln Met Ile Arg Asp Leu Glu Ala Ser Ile Ala Arg Tyr
545                 550                 555                 560

Lys Glu Glu Tyr Ala Val Leu Ile Ser Glu Ala Gln Ala Ile Lys Ala
                565                 570                 575

Asp Leu Ala Ala Val Glu Ala Lys Val Lys Ser Leu Lys Glu Glu Val
            580                 585                 590

Ala Thr Leu Ile Arg Glu Thr Glu Gln Ile Lys Thr Glu Ser Ser Lys
            595                 600                 605

Val Lys Ala Gln Val Gln Ala Leu Glu Ile Glu Val Lys Asp Asn Lys
            610                 615                 620

Thr Lys Val Val Gln Leu Glu Val Glu Val Ala Gln Leu Glu Ser Glu
625                 630                 635                 640

Val Lys Asp Leu Glu
                645

<210> SEQ ID NO 5
<211> LENGTH: 812
<212> TYPE: PRT
<213> ORGANISM: Artificial Sequence
<220> FEATURE:
<223> OTHER INFORMATION: Description of Artificial Sequence: fusion
      protein

<400> SEQUENCE: 5
```

```
Glu Leu Asn Gln Glu Asn Glu Gln Leu Met Glu Asp Tyr Glu Lys Leu
  1               5                  10                  15
Ala Ser Asp Leu Leu Glu Trp Ile Arg Arg Thr Ile Pro Trp Leu Glu
             20                  25                  30
Asn Arg Ala Pro Glu Asn Thr Met Gln Ala Met Gln Gln Lys Leu Glu
         35                  40                  45
Asp Phe Arg Asp Tyr Arg Arg Leu His Lys Pro Pro Lys Val Gln Glu
     50                  55                  60
Lys Cys Gln Leu Glu Ile Asn Phe Asn Thr Leu Gln Thr Lys Leu Arg
 65                  70                  75                  80
Leu Ser Asn Arg Pro Ala Phe Met Pro Ser Glu Gly Lys Met Val Ser
                 85                  90                  95
Asp Ile Asn Asn Ala Trp Gly Leu Glu Gln Ala Glu Lys Gly Tyr
                100                 105                 110
Glu Glu Trp Leu Leu Asn Glu Ile Arg Arg Leu Glu Arg Leu Asp His
             115                 120                 125
Leu Ala Glu Lys Phe Arg Gln Lys Ala Ser Ile His Glu Ser Trp Thr
130                 135                 140
Asp Gly Lys Glu Ala Met Leu Gln Gln Lys Asp Tyr Glu Thr Ala Thr
145                 150                 155                 160
Leu Ser Glu Ile Lys Ala Leu Leu Lys Lys His Glu Ala Phe Glu Ser
                165                 170                 175
Asp Leu Ala Ala His Gln Asp Arg Val Glu Gln Ile Ala Ala Ile Ala
                180                 185                 190
Gln Glu Leu Asn Glu Leu Asp Tyr Tyr Asp Ser Pro Ser Val Asn Ala
            195                 200                 205
Arg Cys Gln Lys Ile Cys Asp Gln Trp Asp Asn Leu Gly Ala Leu Thr
        210                 215                 220
Gln Lys Arg Arg Glu Ala Leu Glu Arg Thr Glu Lys Leu Leu Glu Thr
225                 230                 235                 240
Ile Asp Gln Leu Tyr Leu Glu Tyr Ala Lys Arg Ala Ala Pro Phe Asn
                245                 250                 255
Asn Trp Met Glu Gly Ala Met Glu Asp Leu Gln Asp Thr Phe Ile Val
            260                 265                 270
His Thr Ile Glu Glu Ile Gln Gly Leu Thr Thr Ala His Glu Gln Phe
        275                 280                 285
Lys Ala Thr Leu Pro Asp Ala Asp Lys Glu Arg Gln Ala Ile Leu Gly
290                 295                 300
Ile His Asn Glu Val Ser Lys Ile Val Gln Thr Tyr His Val Asn Met
305                 310                 315                 320
Ala Gly Thr Asn Pro Tyr Thr Thr Ile Thr Pro Gln Glu Ile Asn Gly
                325                 330                 335
Lys Trp Glu His Val Arg Gln Leu Val Pro Arg Arg Asp Gln Ala Leu
            340                 345                 350
Met Glu Glu His Ala Arg Gln Gln Asn Glu Arg Leu Arg Lys Gln
        355                 360                 365
Phe Gly Ala Gln Ala Asn Val Ile Gly Pro Trp Ile Gln Thr Lys Met
370                 375                 380
Glu Glu Ile Gly Arg Ile Ser Ile Glu Met His Gly Thr Leu Glu Asp
385                 390                 395                 400
Gln Leu Asn His Leu Arg Gln Tyr Glu Lys Ser Ile Val Asn Tyr Lys
                405                 410                 415
Pro Lys Ile Asp Gln Leu Glu Gly Asp His Gln Gln Ile Gln Glu Ala
```

```
                   420             425             430
Leu Ile Phe Asp Asn Lys His Thr Asn Tyr Thr Met Glu His Ile Arg
            435                 440                 445
Val Gly Trp Glu Gln Leu Leu Thr Thr Ile Ala Arg Thr Ile Asn Glu
        450                 455                 460
Val Glu Asn Gln Ile Leu Thr Leu Glu Gly Ser Gly Val Ser Lys Gly
465                 470                 475                 480
Glu Glu Leu Phe Thr Gly Val Val Pro Ile Leu Val Glu Leu Asp Gly
                485                 490                 495
Asp Val Asn Gly His Lys Phe Ser Val Ser Gly Glu Gly Glu Gly Asp
            500                 505                 510
Ala Thr Tyr Gly Lys Leu Thr Leu Lys Phe Ile Cys Thr Thr Gly Lys
        515                 520                 525
Leu Pro Val Pro Trp Pro Thr Leu Val Thr Thr Leu Thr Tyr Gly Val
    530                 535                 540
Gln Cys Phe Ser Arg Tyr Pro Asp His Met Lys Gln His Asp Phe Phe
545                 550                 555                 560
Lys Ser Ala Met Pro Glu Gly Tyr Val Gln Glu Arg Thr Ile Phe Phe
                565                 570                 575
Lys Asp Asp Gly Asn Tyr Lys Thr Arg Ala Glu Val Lys Phe Glu Gly
            580                 585                 590
Asp Thr Leu Val Asn Arg Ile Glu Leu Lys Gly Ile Asp Phe Lys Glu
        595                 600                 605
Asp Gly Asn Ile Leu Gly His Lys Leu Glu Tyr Asn Tyr Asn Ser His
    610                 615                 620
Asn Val Tyr Ile Met Ala Asp Lys Gln Lys Asn Gly Ile Lys Val Asn
625                 630                 635                 640
Phe Lys Ile Arg His Asn Ile Glu Asp Ser Gly His His His His
                645                 650                 655
His His His Gly Ser Gly Ala Gly Thr Pro Val Thr Ala Pro Leu Ala
            660                 665                 670
Gly Thr Ile Trp Lys Val Leu Ala Ser Glu Gly Gln Thr Val Ala Ala
        675                 680                 685
Gly Glu Val Leu Leu Ile Leu Glu Ala Met Lys Met Glu Thr Glu Ile
    690                 695                 700
Arg Ala Ala Gln Ala Gly Thr Val Arg Gly Ile Ala Val Lys Ala Gly
705                 710                 715                 720
Asp Ala Val Ala Val Gly Asp Thr Leu Met Thr Leu Ala Gly Ser Gly
                725                 730                 735
Ser His Gly Ser Gly Ser Val Gln Leu Ala Asp His Tyr Gln Gln Asn
            740                 745                 750
Thr Pro Ile Gly Asp Gly Pro Val Leu Leu Pro Asp Asn His Tyr Leu
        755                 760                 765
Ser Thr Gln Ser Ala Leu Ser Lys Asp Pro Asn Glu Lys Arg Asp His
    770                 775                 780
Met Val Leu Leu Glu Phe Val Thr Ala Ala Gly Ile Thr Leu Gly Met
785                 790                 795                 800
Asp Glu Leu Tyr Lys Gly Ser Gly Ser Glu Val Asp
                805                 810

<210> SEQ ID NO 6
<211> LENGTH: 102
<212> TYPE: PRT
<213> ORGANISM: Artificial Sequence
<220> FEATURE:
```

-continued

<223> OTHER INFORMATION: Description of Artificial Sequence: synthetic
     peptide

<400> SEQUENCE: 6

Val Asp Gln Leu Lys Ile Lys Val Glu Gln Leu Lys Glu Lys Val Asn
1               5                   10                  15

Glu Leu Glu Leu Glu Asn Asp Glu Leu Lys Ala Lys Val Asp Asn Leu
            20                  25                  30

Asn Ser Lys Asn Arg Glu Leu Asp Val Lys Asn Glu Gln Ala Asn Gln
        35                  40                  45

Lys Leu Lys Gln Leu Val Gln Asp Val Gln Ala Ala Glu Ile Lys Val
    50                  55                  60

Lys Asp Ala Ser Glu Leu Gln Val Gln Leu Asp Val Arg Asn Lys Glu
65                  70                  75                  80

Ile Ala Val Gln Lys Val Lys Ala His Ala Asp Leu Glu Lys Ala Glu
                85                  90                  95

Pro Ala Ile Ile Glu Gly
            100

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: synthetic
     peptide

<400> SEQUENCE: 7

Ser Glu Ile Leu Asp Arg Ile Lys Pro Leu Arg Glu Glu Val Glu Gln
1               5                   10                  15

Leu Glu Asn Ala Ala Asn Glu Leu Lys Leu Lys Gln Asp Glu Ile Val
            20                  25                  30

Ala Thr Ile Thr Ala Leu Glu Lys Ser Ile Ala Ser Leu Lys Glu Glu
        35                  40                  45

Val Ala Thr Leu Ile Arg Glu Thr Glu Gln Ile Lys Thr Glu Ser Ser
    50                  55                  60

Lys Val Lys Ala Gln Val Gln Ala Leu Glu Ile Glu Val Lys Asp Asn
65                  70                  75                  80

Lys Thr Lys Val Val Gln Leu Glu Val Glu Val Ala Gln Leu Glu Ser
                85                  90                  95

Glu Val Lys Asp Leu Glu
            100

<210> SEQ ID NO 8
<211> LENGTH: 165
<212> TYPE: PRT
<213> ORGANISM: Artificial Sequence
<220> FEATURE:
<223> OTHER INFORMATION: Description of Artificial Sequence: synthetic
     peptide

<400> SEQUENCE: 8

Val Asp Gln Leu Lys Ile Lys Val Glu Gln Leu Lys Glu Lys Val Asn
1               5                   10                  15

Glu Leu Glu Leu Glu Asn Asp Glu Leu Lys Ala Lys Val Asp Asn Leu
            20                  25                  30

Asn Ser Lys Asn Arg Glu Leu Asp Val Lys Asn Glu Gln Ala Asn Gln
        35                  40                  45

Lys Leu Lys Gln Leu Val Gln Asp Val Gln Ala Val Arg Ile Lys Ser
    50                  55                  60

```
Gln Glu Leu Glu Val Lys Asn Ala Ala Asn Asp Lys Leu Lys Lys
 65                  70                  75                  80

Met Val Lys Asp Gln Gln Ala Glu Lys Lys Val Met Ser Gln
                 85                  90                  95

Glu Ile Gln Glu Gln Leu His Lys Gln Glu Val Ile Ala Asp Lys
                100                 105                 110

Gln Met Ser Val Lys Glu Asp Leu Asp Lys Ala Glu Ile Lys Val Lys
        115                 120                 125

Asp Ala Ser Glu Leu Gln Val Gln Leu Asp Val Arg Asn Lys Glu Ile
        130                 135                 140

Ala Val Gln Lys Val Lys Ala His Ala Asp Leu Glu Lys Ala Glu Pro
145                 150                 155                 160

Ala Ile Ile Glu Gly
                165

<210> SEQ ID NO 9
<211> LENGTH: 165
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Ser Glu Ile Leu Asp Arg Ile Lys Pro Leu Arg Glu Val Glu Gln
  1               5                  10                  15

Leu Glu Asn Ala Ala Asn Glu Leu Lys Leu Lys Gln Asp Glu Ile Val
                 20                  25                  30

Ala Thr Ile Thr Ala Leu Glu Lys Ser Ile Ala Ser Leu Arg Asn Glu
         35                  40                  45

Leu Gln Lys Leu Glu Asp Asp Ala Lys Asp Asn Gln Gln Lys Ala Asn
     50                  55                  60

Glu Val Glu Gln Met Ile Arg Asp Leu Glu Ala Ser Ile Ala Arg Tyr
 65                  70                  75                  80

Lys Glu Glu Tyr Ala Val Leu Ile Ser Glu Ala Gln Ala Ile Lys Ala
                 85                  90                  95

Asp Leu Ala Ala Val Glu Ala Lys Val Lys Ser Leu Lys Glu Glu Val
                100                 105                 110

Ala Thr Leu Ile Arg Glu Thr Glu Gln Ile Lys Thr Glu Ser Ser Lys
        115                 120                 125

Val Lys Ala Gln Val Gln Ala Leu Glu Ile Glu Val Lys Asp Asn Lys
        130                 135                 140

Thr Lys Val Val Gln Leu Glu Val Glu Val Ala Gln Leu Glu Ser Glu
145                 150                 155                 160

Val Lys Asp Leu Glu
                165

<210> SEQ ID NO 10
<211> LENGTH: 473
<212> TYPE: PRT
<213> ORGANISM: Artificial Sequence
<220> FEATURE:
<223> OTHER INFORMATION: Description of Artificial Sequence: synthetic
      protein

<400> SEQUENCE: 10

Glu Leu Asn Gln Glu Asn Glu Gln Leu Met Glu Asp Tyr Glu Lys Leu
  1               5                  10                  15
```

-continued

```
Ala Ser Asp Leu Leu Glu Trp Ile Arg Arg Thr Ile Pro Trp Leu Glu
            20                  25                  30

Asn Arg Ala Pro Glu Asn Thr Met Gln Ala Met Gln Gln Lys Leu Glu
        35                  40                  45

Asp Phe Arg Asp Tyr Arg Arg Leu His Lys Pro Pro Lys Val Gln Glu
    50                  55                  60

Lys Cys Gln Leu Glu Ile Asn Phe Asn Thr Leu Gln Thr Lys Leu Arg
65                  70                  75                  80

Leu Ser Asn Arg Pro Ala Phe Met Pro Ser Glu Gly Lys Met Val Ser
                85                  90                  95

Asp Ile Asn Asn Ala Trp Gly Gly Leu Glu Gln Ala Glu Lys Gly Tyr
            100                 105                 110

Glu Glu Trp Leu Leu Asn Glu Ile Arg Arg Leu Glu Arg Leu Asp His
        115                 120                 125

Leu Ala Glu Lys Phe Arg Gln Lys Ala Ser Ile His Glu Ser Trp Thr
    130                 135                 140

Asp Gly Lys Glu Ala Met Leu Gln Gln Lys Asp Tyr Glu Thr Ala Thr
145                 150                 155                 160

Leu Ser Glu Ile Lys Ala Leu Leu Lys Lys His Glu Ala Phe Glu Ser
                165                 170                 175

Asp Leu Ala Ala His Gln Asp Arg Val Glu Gln Ile Ala Ala Ile Ala
            180                 185                 190

Gln Glu Leu Asn Glu Leu Asp Tyr Tyr Asp Ser Pro Ser Val Asn Ala
        195                 200                 205

Arg Cys Gln Lys Ile Cys Asp Gln Trp Asp Asn Leu Gly Ala Leu Thr
    210                 215                 220

Gln Lys Arg Arg Glu Ala Leu Glu Arg Thr Glu Lys Leu Leu Glu Thr
225                 230                 235                 240

Ile Asp Gln Leu Tyr Leu Glu Tyr Ala Lys Arg Ala Ala Pro Phe Asn
                245                 250                 255

Asn Trp Met Glu Gly Ala Met Glu Asp Leu Gln Asp Thr Phe Ile Val
            260                 265                 270

His Thr Ile Glu Glu Ile Gln Gly Leu Thr Thr Ala His Glu Gln Phe
        275                 280                 285

Lys Ala Thr Leu Pro Asp Ala Asp Lys Glu Arg Gln Ala Ile Leu Gly
    290                 295                 300

Ile His Asn Glu Val Ser Lys Ile Val Gln Thr Tyr His Val Asn Met
305                 310                 315                 320

Ala Gly Thr Asn Pro Tyr Thr Thr Ile Thr Pro Gln Glu Ile Asn Gly
                325                 330                 335

Lys Trp Glu His Val Arg Gln Leu Val Pro Arg Arg Asp Gln Ala Leu
            340                 345                 350

Met Glu Glu His Ala Arg Gln Gln Asn Glu Arg Leu Arg Lys Gln
        355                 360                 365

Phe Gly Ala Gln Ala Asn Val Ile Gly Pro Trp Ile Gln Thr Lys Met
    370                 375                 380

Glu Glu Ile Gly Arg Ile Ser Ile Glu Met His Gly Thr Leu Glu Asp
385                 390                 395                 400

Gln Leu Asn His Leu Arg Gln Tyr Glu Lys Ser Ile Val Asn Tyr Lys
                405                 410                 415

Pro Lys Ile Asp Gln Leu Glu Gly Asp His Gln Gln Ile Gln Glu Ala
            420                 425                 430

Leu Ile Phe Asp Asn Lys His Thr Asn Tyr Thr Met Glu His Ile Arg
        435                 440                 445
```

```
Val Gly Trp Glu Gln Leu Leu Thr Thr Ile Ala Arg Thr Ile Asn Glu
    450                 455                 460

Val Glu Asn Gln Ile Leu Thr Leu Glu
465                 470

<210> SEQ ID NO 11
<211> LENGTH: 72
<212> TYPE: PRT
<213> ORGANISM: Artificial Sequence
<220> FEATURE:
<223> OTHER INFORMATION: Description of Artificial Sequence synthetic
      peptide

<400> SEQUENCE: 11

Gly Ala Gly Thr Pro Val Thr Ala Pro Leu Ala Gly Thr Ile Trp Lys
1               5                   10                  15

Val Leu Ala Ser Glu Gly Gln Thr Val Ala Ala Gly Glu Val Leu Leu
                20                  25                  30

Ile Leu Glu Ala Met Lys Met Glu Thr Glu Ile Arg Ala Ala Gln Ala
            35                  40                  45

Gly Thr Val Arg Gly Ile Ala Val Lys Ala Gly Asp Ala Val Ala Val
        50                  55                  60

Gly Asp Thr Leu Met Thr Leu Ala
65                  70

<210> SEQ ID NO 12
<211> LENGTH: 810
<212> TYPE: PRT
<213> ORGANISM: Artificial Sequence
<220> FEATURE:
<223> OTHER INFORMATION: Description of Artificial Sequence: fusion
      protein

<400> SEQUENCE: 12

Thr Ile Asp Gln Leu His Leu Glu Phe Ala Lys Arg Ala Ala Pro Phe
1               5                   10                  15

Asn Asn Trp Met Glu Gly Ala Met Glu Asp Leu Gln Asp Met Phe Ile
                20                  25                  30

Val His Ser Ile Glu Glu Ile Gln Ser Leu Ile Ser Ala His Asp Gln
            35                  40                  45

Phe Lys Ala Thr Leu Pro Glu Ala Asp Gly Glu Arg Gln Ala Ile Leu
        50                  55                  60

Ser Ile Gln Asn Glu Val Glu Lys Val Ile Gln Ser Tyr Ser Met Arg
65                  70                  75                  80

Ile Ser Ala Ser Asn Pro Tyr Ser Thr Val Thr Val Glu Glu Ile Arg
                85                  90                  95

Thr Lys Trp Glu Lys Val Lys Gln Leu Val Pro Gln Arg Asp Gln Ser
            100                 105                 110

Leu Gln Glu Glu Leu Ala Arg Gln His Ala Asn Glu Arg Leu Arg Arg
        115                 120                 125

Gln Phe Ala Ala Gln Ala Asn Val Ile Gly Pro Trp Ile Gln Thr Lys
    130                 135                 140

Met Glu Glu Ile Ala Arg Ser Ser Ile Glu Met Thr Gly Pro Leu Glu
145                 150                 155                 160

Asp Gln Met Asn Gln Leu Lys Gln Tyr Glu Gln Asn Ile Ile Asn Tyr
                165                 170                 175

Lys His Asn Ile Asp Lys Leu Glu Gly Asp His Gln Leu Ile Gln Glu
            180                 185                 190
```

```
Ala Leu Val Phe Asp Asn Lys His Thr Asn Tyr Thr Met Glu His Ile
        195                 200                 205

Arg Val Gly Trp Glu Leu Leu Leu Thr Thr Ile Ala Arg Thr Ile Asn
    210                 215                 220

Glu Val Glu Thr Gln Ile Leu Thr Glu Phe Gly Ser Gly Val Ser Lys
225                 230                 235                 240

Gly Glu Glu Leu Phe Thr Gly Val Val Pro Ile Leu Val Glu Leu Asp
                245                 250                 255

Gly Asp Val Asn Gly His Lys Phe Ser Val Ser Gly Glu Gly Glu Gly
                260                 265                 270

Asp Ala Thr Tyr Gly Lys Leu Thr Leu Lys Phe Ile Cys Thr Thr Gly
            275                 280                 285

Lys Leu Pro Val Pro Trp Pro Thr Leu Val Thr Thr Leu Thr Tyr Gly
        290                 295                 300

Val Gln Cys Phe Ser Arg Tyr Pro Asp His Met Lys Gln His Asp Phe
305                 310                 315                 320

Phe Lys Ser Ala Met Pro Glu Gly Tyr Val Gln Glu Arg Thr Ile Phe
                325                 330                 335

Phe Lys Asp Asp Gly Asn Tyr Lys Thr Arg Ala Glu Val Lys Phe Glu
            340                 345                 350

Gly Asp Thr Leu Val Asn Arg Ile Glu Leu Lys Gly Ile Asp Phe Lys
        355                 360                 365

Glu Asp Gly Asn Ile Leu Gly His Lys Leu Glu Tyr Asn Tyr Asn Ser
    370                 375                 380

His Asn Val Tyr Ile Met Ala Asp Lys Gln Lys Asn Gly Ile Lys Val
385                 390                 395                 400

Asn Phe Lys Ile Arg His Asn Ile Glu Asp Gly Ser Gly His His His
                405                 410                 415

His His His His His Gly Ser Gly Ala Gly Thr Pro Val Thr Ala Pro
            420                 425                 430

Leu Ala Gly Thr Ile Trp Lys Val Leu Ala Ser Glu Gly Gln Thr Val
        435                 440                 445

Ala Ala Gly Glu Val Leu Leu Ile Leu Glu Ala Met Lys Met Glu Thr
    450                 455                 460

Glu Ile Arg Ala Ala Gln Ala Gly Thr Val Arg Gly Ile Ala Val Lys
465                 470                 475                 480

Ala Gly Asp Ala Val Ala Val Gly Asp Thr Leu Met Thr Leu Ala Gly
                485                 490                 495

Ser Gly Ser His Gly Ser Gly Ser Val Gln Leu Ala Asp His Tyr Gln
            500                 505                 510

Gln Asn Thr Pro Ile Gly Asp Gly Pro Val Leu Leu Pro Asp Asn His
        515                 520                 525

Tyr Leu Ser Thr Gln Ser Ala Leu Ser Lys Asp Pro Asn Glu Lys Arg
    530                 535                 540

Asp His Met Val Leu Leu Glu Phe Val Thr Ala Ala Gly Ile Thr Leu
545                 550                 555                 560

Gly Met Asp Glu Leu Tyr Lys Gly Ser Gly Ser Val Asp Asn Gln Glu
                565                 570                 575

Asn Glu Arg Leu Met Glu Glu Tyr Glu Arg Leu Ala Ser Glu Leu Leu
            580                 585                 590

Glu Trp Ile Arg Arg Thr Ile Pro Trp Leu Glu Asn Arg Thr Pro Glu
        595                 600                 605

Lys Thr Met Gln Ala Met Gln Lys Lys Leu Glu Asp Phe Arg Asp Tyr
    610                 615                 620
```

Arg Arg Lys His Lys Pro Pro Lys Val Gln Glu Lys Cys Gln Leu Glu
625                 630                 635                 640

Ile Asn Phe Asn Thr Leu Gln Thr Lys Leu Arg Ile Ser Asn Arg Pro
            645                 650                 655

Ala Phe Met Pro Ser Glu Gly Lys Met Val Ser Asp Ile Ala Gly Ala
            660                 665                 670

Trp Gln Arg Leu Glu Gln Ala Glu Lys Gly Tyr Glu Glu Trp Leu Leu
        675                 680                 685

Asn Glu Ile Arg Arg Leu Glu Arg Leu Glu His Leu Ala Glu Lys Phe
    690                 695                 700

Arg Gln Lys Ala Ser Thr His Glu Gln Trp Ala Tyr Gly Lys Glu Gln
705                 710                 715                 720

Ile Leu Leu Gln Lys Asp Tyr Glu Ser Ala Ser Leu Thr Glu Val Arg
                725                 730                 735

Ala Met Leu Arg Lys His Glu Ala Phe Glu Ser Asp Leu Ala Ala His
            740                 745                 750

Gln Asp Arg Val Glu Gln Ile Ala Ala Ile Ala Gln Glu Leu Asn Glu
        755                 760                 765

Leu Asp Tyr His Asp Ala Ala Ser Val Asn Asp Arg Cys Gln Lys Ile
    770                 775                 780

Cys Asp Gln Trp Asp Ser Leu Gly Thr Leu Thr Gln Lys Arg Arg Glu
785                 790                 795                 800

Ala Leu Glu Arg Thr Glu Lys Leu Leu Glu
                805                 810

<210> SEQ ID NO 13
<211> LENGTH: 235
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Thr Ile Asp Gln Leu His Leu Glu Phe Ala Lys Arg Ala Ala Pro Phe
1               5                   10                  15

Asn Asn Trp Met Glu Gly Ala Met Glu Asp Leu Gln Asp Met Phe Ile
            20                  25                  30

Val His Ser Ile Glu Glu Ile Gln Ser Leu Ile Ser Ala His Asp Gln
        35                  40                  45

Phe Lys Ala Thr Leu Pro Glu Ala Asp Gly Glu Arg Gln Ala Ile Leu
    50                  55                  60

Ser Ile Gln Asn Glu Val Glu Lys Val Ile Gln Ser Tyr Ser Met Arg
65                  70                  75                  80

Ile Ser Ala Ser Asn Pro Tyr Ser Thr Val Thr Val Glu Glu Ile Arg
                85                  90                  95

Thr Lys Trp Glu Lys Val Lys Gln Leu Val Pro Gln Arg Asp Gln Ser
            100                 105                 110

Leu Gln Glu Glu Leu Ala Arg Gln His Ala Asn Glu Arg Leu Arg Arg
        115                 120                 125

Gln Phe Ala Ala Gln Ala Asn Val Ile Gly Pro Trp Ile Gln Thr Lys
    130                 135                 140

Met Glu Glu Ile Ala Arg Ser Ser Ile Glu Met Thr Gly Pro Leu Glu
145                 150                 155                 160

Asp Gln Met Asn Gln Leu Lys Gln Tyr Glu Gln Asn Ile Ile Asn Tyr
                165                 170                 175

```
Lys His Asn Ile Asp Lys Leu Glu Gly Asp His Gln Leu Ile Gln Glu
            180                 185                 190

Ala Leu Val Phe Asp Asn Lys His Thr Asn Tyr Thr Met Glu His Ile
        195                 200                 205

Arg Val Gly Trp Glu Leu Leu Thr Thr Ile Ala Arg Thr Ile Asn
    210                 215                 220

Glu Val Glu Thr Gln Ile Leu Thr Glu Phe Gly
225                 230                 235

<210> SEQ ID NO 14
<211> LENGTH: 240
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Ser Val Asp Asn Gln Glu Asn Glu Arg Leu Met Glu Glu Tyr Glu Arg
1               5                   10                  15

Leu Ala Ser Glu Leu Leu Glu Trp Ile Arg Arg Thr Ile Pro Trp Leu
            20                  25                  30

Glu Asn Arg Thr Pro Glu Lys Thr Met Gln Ala Met Gln Lys Lys Leu
        35                  40                  45

Glu Asp Phe Arg Asp Tyr Arg Arg Lys His Lys Pro Pro Lys Val Gln
    50                  55                  60

Glu Lys Cys Gln Leu Glu Ile Asn Phe Asn Thr Leu Gln Thr Lys Leu
65                  70                  75                  80

Arg Ile Ser Asn Arg Pro Ala Phe Met Pro Ser Glu Gly Lys Met Val
                85                  90                  95

Ser Asp Ile Ala Gly Ala Trp Gln Arg Leu Glu Gln Ala Glu Lys Gly
            100                 105                 110

Tyr Glu Glu Trp Leu Leu Asn Glu Ile Arg Arg Leu Glu Arg Leu Glu
        115                 120                 125

His Leu Ala Glu Lys Phe Arg Gln Lys Ala Ser Thr His Glu Gln Trp
    130                 135                 140

Ala Tyr Gly Lys Glu Gln Ile Leu Leu Gln Lys Asp Tyr Glu Ser Ala
145                 150                 155                 160

Ser Leu Thr Glu Val Arg Ala Met Leu Arg Lys His Glu Ala Phe Glu
                165                 170                 175

Ser Asp Leu Ala Ala His Gln Asp Arg Val Glu Gln Ile Ala Ala Ile
            180                 185                 190

Ala Gln Glu Leu Asn Glu Leu Asp Tyr His Asp Ala Ala Ser Val Asn
        195                 200                 205

Asp Arg Cys Gln Lys Ile Cys Asp Gln Trp Asp Ser Leu Gly Thr Leu
    210                 215                 220

Thr Gln Lys Arg Arg Glu Ala Leu Glu Arg Thr Glu Lys Leu Leu Glu
225                 230                 235                 240
```